United States Patent [19]

Dale et al.

[11] Patent Number: 4,920,213

[45] Date of Patent: Apr. 24, 1990

[54] METHOD AND COMPOSITIONS USEFUL IN PREVENTING EQUINE INFLUENZA

[75] Inventors: Beverly Dale, Mt. View; Barbara Cordell, San Francisco, both of Calif.

[73] Assignee: Biotechnology Research Partners, Ltd., Mountain View, Calif.

[21] Appl. No.: 888,250

[22] Filed: Jul. 21, 1986

Related U.S. Application Data

[63] Continuation-in-part of Ser. No. 747,020, Jun. 20, 1985, Pat. No. 4,361,191.

[51] Int. Cl.[5] .................. C12P 21/00; C12P 21/02; C07H 15/12
[52] U.S. Cl. .................. 536/27; 435/172.3; 435/69.1; 435/69.3; 435/320; 435/200; 435/201; 435/235; 935/12; 935/14
[58] Field of Search ............. 435/68, 70, 172.3, 91, 435/235, 320, 238, 948, 235, 200, 201; 935/18, 12, 27, 65, 14; 536/27

[56] References Cited

PUBLICATIONS

Biok et al, *Virology*, vol. 121, pp. 211–229, 1982, "Sequence Variation at the 3'enl of the Neuraminidaze Gene from 39 Influenza Type A Virses".

Racaniello et al, *Proc Hutl Acad Sci.*, vol. 78 (8), pp. 4887–4891, Aug. 1981, "Molecular Cloning of Polio Virus CDNA and Determination of the Complete Nicleotide Sequence of the Viral Germs".

Air et al, *Proc Natl Acad Sci*, vol. 78, pp. 7639–7643, 1981, "Sequence Relationships Between the Hemaggletion Genes of Twelve Subtypes of Influenza A Virus".

Lonberg et al, *Proc Natl Acad Sci*, 1983, vol. 80, pp. 3661–3665.

Daniels et al, *J Gen Virol*, vol. 66, pp. 457–464, Mar. 1985, "Amino Acid Sequences of Haemagglutatinins of Influenza Viruses of the $H_3$ Subtype Isolated from Horses".

Rhode et al, *Virology*, vol. 79(2), pp. 393–404, 1977, "Biochemical Studies on Influenza Viruses Comparative Analysis of Equine 2 Virus and Virus N Genes and Gene Products".

Schotissek et al, *Virology*, vol. 79, pp. 330–336, 1977, "Correlation between Base Sequence Homology of RNA Segment 4 and Antiogenicity of the Hemagglutinin of Influenza Viruses".

Souihoua et al, *Acta Birol.*, *1958, vol. 2, pp. 52–61.*

Primary Examiner—Robin Teskin
Attorney, Agent, or Firm—Irell & Manella

[57] ABSTRACT

Recombinant vaccines for immunizing horses against equine influenza virus (EIV) are disclosed. The DNA sequences encoding the hemagglutinin (HA) and neuraminidase (NA) glycoproteins from the two strains of EIV currently infective in horses are used to construct vaccinia carried vaccines, to design synthetic peptides for primer and booster administration, and to permit recombinant synthesis of HA and/or NA protein based vaccines. These DNA sequences also provide probes useful for preparing similar vaccines from fresh isolates of new strains generated by genetic drift.

2 Claims, 14 Drawing Sheets

EIV - A1 hemagglutinin (H7)

```
                                                        50
      ctgcaggggg ggggggggg gggagcaaaa gcaggggata cata ATG AAC ACT CAA ATT
                                                      MET Asn Thr Gln Ile
                                                           ┌──► HA1
                                                           │100
CTA ATA TTA GCC ATT TCG GCA TTC CTC TGT GTA CGT GCA GAT AAA ATC TGC CTA
Leu Ile Leu Ala Ile Ser Ala Phe Leu Cys Val Arg Ala Asp Lys Ile Cys Leu
                                                                  ▲
                      150
GGA CAT CAT GCT GTG TCT AAT GGA ACC AAA GTA GAC ACC CTT ACT GAA AAG GGA
Gly His His Ala Val Ser Asn Gly Thr Lys Val Asp Thr Leu Thr Glu Lys Gly 200
ATA GAA GTT GTC AAT GCA ACA GAA ACA GTT GAA CAA AAA AAC ATC CCC AAG ATC
Ile Glu Val Val Asn Ala Thr Glu Thr Val Glu Gln Lys Asn Ile Pro Lys Ile 250
TGC TCA AAA GGG AAA CAG ACT ATT GAC CTT GGT CAA TGT GGA TTA CTA GGG ACC
Cys Ser Lys Gly Lys Gln Thr Ile Asp Leu Gly Gln Cys Gly Leu Leu Gly Thr
 ▲                                              ▲
                          300
ACT ATT GGT CCC CCC CAA TGC GAC CAA TTT CTT GAA TTC TCT GCT AAT TTA ATA
Thr Ile Gly Pro Pro Gln Cys Asp Gln Phe Leu Glu Phe Ser Ala Asn Leu Ile
                          ▲
                      350
ATT GAG AGA AGA GAA GGT GAT GAC ATT TGT TAT CCA GGC AAA TTT GAC AAT GAA
Ile Glu Arg Arg Glu Gly Asp Asp Ile Cys Tyr Pro Gly Lys Phe Asp Asn Glu
                                      ▲
              400
GAA ACA TTG AGA CAA ATA CTC AGA AAA TCC GGA GGA ATT AAA AAG GAG AAT ATG
Glu Thr Leu Arg Gln Ile Leu Arg Lys Ser Gly Gly Ile Lys Lys Glu Asn MET 450
GGA TTC ACA TAT ACC GGA GTG AGA ACC GAT GGA GAG ACT AGC GCC TGT AGA AGG
Gly Phe Thr Tyr Thr Gly Val Arg Thr Asp Gly Glu Thr Ser Ala Cys Arg Arg
                                                              ▲
          500
TCA AGA TCT TCC TTT TAT GCA GAA ATG AAA TGG CTC CTA TCC AAC ACA GAC AAT
Ser Arg Ser Ser Phe Tyr Ala Glu MET Lys Trp Leu Leu Ser Asn Thr Asp Asn 550
GGG GTA TTC CCA CAA ATG ACA AAA TCC TAC AAG AAC ACT AAG AGG GAG CCA GCT
Gly Val Phe Pro Gln MET Thr Lys Ser Tyr Lys Asn Thr Lys Arg Glu Pro Ala 600                                                                 650
CTG ATA ATC TGG GGA ATC CAC CAC TCA GGA TCA ACC GCT GAA CAG ACT AGA TTG
Leu Ile Ile Trp Gly Ile His His Ser Gly Ser Thr Ala Glu Gln Thr Arg Leu 700
TAT GGA AGC GGA AAC AAG TTG ATA ACA GTT TGG AGT TCC AAA TAC CAA CAA TCT
Tyr Gly Ser Gly Asn Lys Leu Ile Thr Val Trp Ser Ser Lys Tyr Gln Gln Ser
```

FIG. 1-1

```
                                                            750
TTT GCC CCA AGC CCT GGA CCA AGG CCG CAA ATA AAT GGC CAA TCA GGA AGA ATT
Phe Ala Pro Ser Pro Gly Pro Arg Pro Gln Ile Asn Gly Gln Ser Gly Arg Ile

800
GAC TTT TAC TGG CTG ATG TTA GAT CCC AAT GAT ACT GTT ACT TTC AGT TTT AAT
Asp Phe Tyr Trp Leu MET Leu Asp Pro Asn Asp Thr Val Thr Phe Ser Phe Asn

850
GGG GCC TTT ATA GCA CCT GAC CGC GCC AGT TTT CTA AGA GGT AAA TCT CTA GGA
Gly Ala Phe Ile Ala Pro Asp Arg Ala Ser Phe Leu Arg Gly Lys Ser Leu Gly

900
ATT CAG AGT GAC GCA CAA CTT GAC AAC AAT TGT GAA GGT GAA TGT TAT CAT ATT
Ile Gln Ser Asp Ala Gln Leu Asp Asn Asn Cys Glu Gly Glu Cys Tyr His Ile
                                        ▲               ▲
                    950
GGA GGT ACT ATA ATT AGC AAC TTG CCC TTT CAA AAC ATT AAT AGC AGA GCA ATT
Gly Gly Thr Ile Ile Ser Asn Leu Pro Phe Gln Asn Ile Asn Ser Arg Ala Ile

1000
GGG AAA TGC CCC AGA TAC GTA AAG CAA AAA AGC TTA ATG CTA GCA ACC GGA ATG
Gly Lys Cys Pro Arg Tyr Val Lys Gln Lys Ser Leu MET Leu Ala Thr Gly MET
    ▲                   HA1
                    1050    ┌─┐
AAA AAT GTT CCT GAA AAT TCT ACA CAC AAA CAG TTA ACT CAT CAC ATG CGC AAA
Lys Asn Val Pro Glu Asn Ser Thr His Lys Gln Leu Thr His His MET Arg Lys
                            ↑
            ┌─►HA2 1100        clip?
AAA AGA GGT TTA TTT GGT GCA ATA GCA GGA TTT ATT GAA AAT GGA TGG GAA GGA
Lys Arg Gly Leu Phe Gly Ala Ile Ala Gly Phe Ile Glu Asn Gly Trp Glu Gly
    ↑└──────── conserved HA2 NH2 terminus ─────────┘
    clip 1150
TTA ATA GAT GGA TGG TAT GGA TAC AGA CAT CAG AAT GCA CAA GGA GAA GGA ACT
Leu Ile Asp Gly Trp Tyr Gly Tyr Arg His Gln Asn Ala Gln Gly Glu Gly Thr 1200
GCT GCA GAC TAC AAA AGT ACA CAA TCT GCT ATC AAT CAA ATA ACC GGG AAA TTA
Ala Ala Asp Tyr Lys Ser Thr Gln Ser Ala Ile Asn Gln Ile Thr Gly Lys Leu 1250                                                    1300
AAC AGA CTA ATA GAA AAA ACC AAC CAG CAA TTT GAA CTA ATA GAT AAT AAA TTC
Asn Arg Leu Ile Glu Lys Thr Asn Gln Gln Phe Glu Leu Ile Asp Asn Lys Phe 1350
AAT GAA ATA GAA AAG CAA ATT GGC AAT GTT ATT AAC TGG ACT AGA GAT TCT ATC
Asn Glu Ile Glu Lys Gln Ile Gly Asn Val Ile Asn Trp Thr Arg Asp Ser Ile 1400
ATC GAA GTA TGG TCA TAT AAT GCA GAA TTC CTC GTG GCA GTG GAG AAT CAA CAC
Ile Glu Val Trp Ser Tyr Asn Ala Glu Phe Leu Val Ala Val Glu Asn Gln His 1450
ACT ATT GAT TCA ACT GAT TCA GAG ATG AAC AAA TTA TAT GAA AAG GTA AGA AGA
Thr Ile Asp Ser Thr Asp Ser Glu MET Asn Lys Leu Tyr Glu Lys Val Arg Arg

FIG. 1-2
```

```
                                              1500
CAG CTG AGA GAA AAT GCT GAG GAA GAT GGT AAT GGC TGT TTT GAA ATA TTC CAC
Gln Leu Arg Glu Asn Ala Glu Glu Asp Gly Asn Gly Cys Phe Glu Ile Phe His
                                                          ▲
                                    1550
CAA TGT GAC AAT GAT TGC ATG GCC AGC ATT AGA AAC AAT ACA TAT GAT CAT AAA
Gln Cys Asp Asn Asp Cys MET Ala Ser Ile Arg Asn Asn Thr Tyr Asp His Lys
 ▲           ▲
                                1600
AAA TAC AGA AAG GAG GCA ATA CAA AAC AGA ATT CAG ATT GAT GCA GTA AAG TTG
Lys Tyr Arg Lys Glu Ala Ile Gln Asn Arg Ile Gln Ile Asp Ala Val Lys Leu
                        1650
AGC AGC GGT TAC AAA GAT ATA ATA CTT TGG TTT AGC TTC GGG GCA TCA TGT TTC
Ser Ser Gly Tyr Lys Asp Ile Ile Leu Trp Phe Ser Phe Gly Ala Ser Cys Phe
                                                                  ▲
                1700
TTA TTT CTT GCC ATT GCA ATG GTT CTT GCT TTC ATA TGC ATA AAA AAT GGA AAC
Leu Phe Leu Ala Ile Ala MET Val Leu Ala Phe Ile Cys Ile Lys Asn Gly Asn
                       HA2◄┐                                ▲
            1750
ATG CGG TGC ACT ATT TGT ATA TAA gtt tgaaaaaaca cccttgtttt ctactccccc
MET Arg Cys Thr Ile Cys Ile  .
 ▲           ▲
       1808
cccccccccc ccctgcag
```

FIG. 1-3

EIV - A2 hemagglutinin (H3)

```
                                                       50
ctgcagggggg gggggggggg ggggagcaaa agcaggggat atttctgtca atc ATG AAG ACA
                                                       MET Lys Thr
                                    AccI     ┌─►HA1
                                      ↓   100
ACC ATT ATT TTG ATA CTA CTG ACC CAT TGG GTC TAC AGT CAA AAC CCA ACC AGT
Thr Ile Ile Leu Ile Leu Leu Thr His Trp Val Tyr Ser Gln Asn Pro Thr Ser 150
GGC AAC AAC ACA GCC ACA CTA TGT CTG GGA CAC CAT GCA GTA GCA AAT GGA ACA
Gly Asn Asn Thr Ala Thr Leu Cys Leu Gly His His Ala Val Ala Asn Gly Thr
                             ▲      200
TTG GTA AAA ACA ATA ACT GAT GAC CAA ATT GAG GTG ACA AAT GCT ACT GAA TTA
Leu Val Lys Thr Ile Thr Asp Asp Gln Ile Glu Val Thr Asn Ala Thr Glu Leu 250
GTT CAG AGC ACT TCA ATA GGG AAA ATA TGC AAC AAC CCA TAT AGG GTT CTA GAT
Val Gln Ser Thr Ser Ile Gly Lys Ile Cys Asn Asn Pro Tyr Arg Val Leu Asp
                                    ▲
                      300
GGA AGA AAC TGC ACA TTA ATA GAT GCA ATG CTA GGA GAT CCC CAC TGT GAT GTT
Gly Arg Asn Cys Thr Leu Ile Asp Ala MET Leu Gly Asp Pro His Cys Asp Val
             ▲                                                  ▲
                350
TTT CAG TAT GAG AAT TGG GAC CTC TTC ATA GAA AGA AGC AGC GCT TTC AGC AAT
Phe Gln Tyr Glu Asn Trp Asp Leu Phe Ile Glu Arg Ser Ser Ala Phe Ser Asn 400
TGC TAC CCA TAT GAC ATC CCT GAC TAT GCA TCG CTC CGG TCT ATT GTG GCA TCT
Cys Tyr Pro Tyr Asp Ile Pro Asp Tyr Ala Ser Leu Arg Ser Ile Val Ala Ser
▲
          450
TCA GGA ACA TTA GAA TTC ACA GCA GAG GGA TTC ACA TGG ACA GGT GTC ACT CAA
Ser Gly Thr Leu Glu Phe Thr Ala Glu Gly Phe Thr Trp Thr Gly Val Thr Gln 500
AAC GGA AGA AGT GGA GCC TGC AGA AGG GGG TCA GCC GAT AGT TTC TTT AGC CGA
Asn Gly Arg Ser Gly Ala Cys Arg Arg Gly Ser Ala Asp Ser Phe Phe Ser Arg
                         ▲
550                                                               600
CTG AAT TGG CTA ACA AAA TCT GGA AAT TCT TAC CCC ACA TTG AAT GTA ACA ATG
Leu Asn Trp Leu Thr Lys Ser Gly Asn Ser Tyr Pro Thr Leu Asn Val Thr MET
                                                            650
CCT AAC AAT AAC AAT TTC GAT AAA CTA TAC ATC TGG GGG ATC CAT CAC CCG AGC
Pro Asn Asn Asn Asn Phe Asp Lys Leu Tyr Ile Trp Gly Ile His His Pro Ser
                                              700
ACA AAC AAT GAG CAG ACA AAA TTG TAT ATC CAA GAA TCA GGG CGA GTA ACA GTC
Thr Asn Asn Glu Gln Thr Lys Leu Tyr Ile Gln Glu Ser Gly Arg Val Thr Val
```

FIG. 2-1

```
                                                    750
TCA ACA AAA AGA AGT CAA CAA ACA ATA ATC CCC AAC ATC GGA TCT AGA CCG TGG
Ser Thr Lys Arg Ser Gln Gln Thr Ile Ile Pro Asn Ile Gly Ser Arg Pro Trp

800
GTC AGG GGT CAA TCA GGC AGG ATA AGC ATA TAT TGG ACC ATT GTG AAA CCT GGA
Val Arg Gly Gln Ser Gly Arg Ile Ser Ile Tyr Trp Thr Ile Val Lys Pro Gly

850
GAT ATC CTA ATG ATA AAC AGT AAT GGC AAC TTA GTT GCA CCG CGG GGA TAT TTT
Asp Ile Leu MET Ile Asn Ser Asn Gly Asn Leu Val Ala Pro Arg Gly Tyr Phe

900
AAA ATG CGA ACA GGG AAA AGC TCT GTA ATG AGA TCA GAT GCA CCC ATA GAC ACT
Lys MET Arg Thr Gly Lys Ser Ser Val MET Arg Ser Asp Ala Pro Ile Asp Thr

950
TGT GTG TCC GAG TGT ATT ACA CCA AAT GGA AGC ATC CCC AAC GAC AAA CCA TTT
Cys Val Ser Glu Cys Ile Thr Pro Asn Gly Ser Ile Pro Asn Asp Lys Pro Phe
▲         ▲
          1000
CAA AAT GTG AAC AAA GTT ACA TAT GGA AAA TGC CCC AAG TAT ATC AAG CAG AAT
Gln Asn Val Asn Lys Val Thr Tyr Gly Lys Cys Pro Lys Tyr Ile Lys Gln Asn
                                      ▲           HA1◄──┐ ┌─►HA2
             1050
ACT TTG AAG CTG GCC ACT GGG ATG AGG AAT GTA CCA GAA AAG CAA ATC AGA GGA
Thr Leu Lys Leu Ala Thr Gly MET Arg Asn Val Pro Glu Lys Gln Ile Arg Gly
                                                                   clip
         1100
ATC TTT GGA GCA ATA GCG GGA TTC ATA GAA AAC GGC TGG GAA GGA ATG GTT GAT
Ile Phe Gly Ala Ile Ala Gly Phe Ile Glu Asn Gly Trp Glu Gly MET Val Asp
─conserved HA2 NH₂ terminus─────────────┘
      1150
GGG TGG TAT GGA TTC CGA TAT CAG AAT TCG GAA GGA ACA GGA CAA GCT GCA GAT
Gly Trp Tyr Gly Phe Arg Tyr Gln Asn Ser Glu Gly Thr Gly Gln Ala Ala Asp 1200                                                           1250
CTA AAG AGC ACT CAA GCA GCC ATC GAC CAG ATC AAT GGA AAA TTG AAC AGA GTG
Leu Lys Ser Thr Gln Ala Ala Ile Asp Gln Ile Asn Gly Lys Leu Asn Arg Val 1300
ATT GAA AGG ACC AAT GAG AAA TTC CAT CAA ATA GAG AAG GAA TTC TCA GAA GTA
Ile Glu Arg Thr Asn Glu Lys Phe His Gln Ile Glu Lys Glu Phe Ser Glu Val 1350
GAA GGG AGA ATC CAG GAC TTG GAG AAG TAT GTA GAA GAC ACC AAA ATA GAC CTA
Glu Gly Arg Ile Gln Asp Leu Glu Lys Tyr Val Glu Asp Thr Lys Ile Asp Leu 1400
TGG TCC TAC AAT GCA GAG TTA CTG GTG GCT CTA GAA AAT CAA CAT ACG ATT GAC
Trp Ser Tyr Asn Ala Glu Leu Leu Val Ala Leu Glu Asn Gln His Thr Ile Asp 1450
TTA ACA GAT GCA GAA ATG AAT AAA TTA TCC GAG AAG ACT AGG CGC CAG TTA AGA
Leu Thr Asp Ala Glu MET Asn Lys Leu Ser Glu Lys Thr Arg Arg Gln Leu Arg
```

FIG. 2-2

```
                                            1500
GAA AAC GCG GAA GAC ATG GGG GGT GGA TGT TTC AAG ATT TAT CAC AAA TGT GAT
Glu Asn Ala Glu Asp MET Gly Gly Gly Cys Phe Lys Ile Tyr His Lys Cys Asp
                                 ▲                                   ▲
                              1550
AAT GCA TGC ATT GGA TCA ATA AGA AAT GGG ACA TAT GAC CAT TAC ATA TAC AGA
Asn Ala Cys Ile Gly Ser Ile Arg Asn Gly Thr Tyr Asp His Tyr Ile Tyr Arg
        ▲
                          1600
GAT GAA GCA TTA AAC AAC CGA TTT CAA ATT AAA GGT GTT GAA TTG AAA TCA GGC
Asp Glu Ala Leu Asn Asn Arg Phe Gln Ile Lys Gly Val Glu Leu Lys Ser Gly

1650
TAC AAA GAT TGG ATA CTG TGG ATT TCA TTC GCC ATA TCA TGC TTC TTA ATT TGC
Tyr Lys Asp Trp Ile Leu Trp Ile Ser Phe Ala Ile Ser Cys Phe Leu Ile Cys
                                             Bgl1 ▲                   ▲
                    1700
GTT GTT CTA TTG GGT TTC ATC ATG TGG GCT TGC CAA AAA GGC AAC ATC AGA TGC
Val Val Leu Leu Gly Phe Ile MET Trp Ala Cys Gln Lys Gly Asn Ile Arg Cys
     HA2◄─┐                                  ▲                        ▲
          1750                                                      1797
AAC ATT TGC ATT TGA gtaaactga tagttaaaaa aaaaaaaaaa cccccccccc cctgcag
Asn Ile Cys Ile  .
▲
```

FIG. 2-3

EIV - A1 neuraminidase (n7)

```
                                                        50
ctgcagggggg ggggggggggg ggtttttttt tttttagcaa aagcagggta attttgaa ATG AAT
                                                                 MET Asn 100
CCT AAT CAA AAA CTC TTT GCA TCA TCC GGA ATA GCA ATA GTG CTA GGA ATA ATA
Pro Asn Gln Lys Leu Phe Ala Ser Ser Gly Ile Ala Ile Val Leu Gly Ile Ile 150
AAT CTT CTC ATA GGA ATA TCC AAT ATG AGT TTA AAT ATA TCT CTA TAT TCA AAA
Asn Leu Leu Ile Gly Ile Ser Asn MET Ser Leu Asn Ile Ser Leu Tyr Ser Lys 200
GGG GAA AGC CAC AAG AAT AAT AAC CTA ACA TGC ACA AAT ATC AAC CAG AAT GAT
Gly Glu Ser His Lys Asn Asn Asn Leu Thr Cys Thr Asn Ile Asn Gln Asn Asp 250
ACC ACC ATG GTA AAC ACG TAC ATC AAT AAC GCA ACA ATA ATT GAC AAA AGT ACA
Thr Thr MET Val Asn Thr Tyr Ile Asn Asn Ala Thr Ile Ile Asp Lys Ser Thr 300
AAA ATA GAA AAC CCT GGT TAT CTA CTG CTG AAC AAA AGT CTA TGC AAC GTT GAA
Lys Ile Glu Asn Pro Gly Tyr Leu Leu Leu Asn Lys Ser Leu Cys Asn Val Glu 350
GGA TGG GTT GTA ATA GCA AAG GAC AAT GCG ATT AGA TTT GGA GAA AGC GAA CAA
Gly Trp Val Val Ile Ala Lys Asp Asn Ala Ile Arg Phe Gly Glu Ser Glu Gln 400
ATC ATA GTA ACT AGA GAA CCT TAT GTC TCA TGT GAT CCT CTA AGT TGC AAA ATG
Ile Ile Val Thr Arg Glu Pro Tyr Val Ser Cys Asp Pro Leu Ser Cys Lys MET 450
TAT GCT CTA CAC CAA GGT ACT ACA ATC AGA AAC AAG CAT TCA AAT AGT ACC ACA
Tyr Ala Leu His Gln Gly Thr Thr Ile Arg Asn Lys His Ser Asn Ser Thr Thr 500                                                             550
CAC GAC AGA ACA GCC TTC CGA GGG CTC ATT TCT ACT CCA TTA GGT AGC CCC CCA
His Asp Arg Thr Ala Phe Arg Gly Leu Ile Ser Thr Pro Leu Gly Ser Pro Pro 600
ACA GTG AGC AAC AGT GAA TTC ATA TGT GTT GGG TGG TCA AGC ACA AGC TGC CAT
Thr Val Ser Asn Ser Glu Phe Ile Cys Val Gly Trp Ser Ser Thr Ser Cys His 650
GAT GGG GTA AAC AGG ATG ACA ATT TGT GTA CAA GGA GAC AAT GAA AAT GCT ACT
Asp Gly Val Asn Arg MET Thr Ile Cys Val Gln Gly Asp Asn Glu Asn Ala Thr 700
GCA ACA GTG TAT TAC AAC AAG AGA CTT ACA ACC ACT ATT AAA ACA TGG GCT AAA
Ala Thr Val Tyr Tyr Asn Lys Arg Leu Thr Thr Thr Ile Lys Thr Trp Ala Lys
```

FIG. 3-1

```
                                              750
AAC ATT TTA AGA ACC CAA GAG TCT GAA TGT GTT TGT CAT AAC AGC ACT TGT GTA
Asn Ile Leu Arg Thr Gln Glu Ser Glu Cys Val Cys His Asn Ser Thr Cys Val

800
GTG GTA ATG ACT GAT GGG CCC GCA AAT AAC CAG GCG TTC ACA AAA GTA ATA TAC
Val Val MET Thr Asp Gly Pro Ala Asn Asn Gln Ala Phe Thr Lys Val Ile Tyr

850
TTT CAT AAA GGA ATG ATA ATA AAA GAA GAA TCA CTA AAA GGT TCA GCC AAA CAC
Phe His Lys Gly MET Ile Ile Lys Glu Glu Ser Leu Lys Gly Ser Ala Lys His

900
ATA GAA GAA TGT TCT TGT TAT GGT CAT AAT CAA AGA GTG ACT TGT GTC TGC AGA
Ile Glu Glu Cys Ser Cys Tyr Gly His Asn Gln Arg Val Thr Cys Val Cys Arg

950
GAC AAC TGG CAG GGT GCA AAT AGA CCT ATT ATA GAG ATT GAC ATG AAT AAA TTG
Asp Asn Trp Gln Gly Ala Asn Arg Pro Ile Ile Glu Ile Asp MET Asn Lys Leu

1000
GAA CAT ACA AGT AGA TAT ATA TGC ACA GGG GTA TTA ACA GAC ACC AGT AGA CCC
Glu His Thr Ser Arg Tyr Ile Cys Thr Gly Val Leu Thr Asp Thr Ser Arg Pro

1050
AAG GAT AAA ACA ATA GGG GAA TGC TTC AAT CCT ATT ACT GGA AGC CCT GGT GCA
Lys Asp Lys Thr Ile Gly Glu Cys Phe Asn Pro Ile Thr Gly Ser Pro Gly Ala

1100
CCA GGG ATA AAA GGT TTC GGA TTC CTA AAT GAG GAT AAT ACT TGG CTA GGG AGA
Pro Gly Ile Lys Gly Phe Gly Phe Leu Asn Glu Asp Asn Thr Trp Leu Gly Arg

1150
ACA ATC AGC CCC AGA TTG AGG AGT GGA TTT GAA ATG CTG AAG ATA CCT AAT GCT
Thr Ile Ser Pro Arg Leu Arg Ser Gly Phe Glu MET Leu Lys Ile Pro Asn Ala 1200                                                              1250
GGG ACT GAC CCA GAG TCC AAA ATA AAA GAA AGA CAA GAA ATA GTT AGT AAT GAC
Gly Thr Asp Pro Glu Ser Lys Ile Lys Glu Arg Gln Glu Ile Val Ser Asn Asp

1300
AAT TGG TCA GGC TAT TCC GGA AGT TTC ATT GAT TAT TGG AAT GAC AAC AGT GAA
Asn Trp Ser Gly Tyr Ser Gly Ser Phe Ile Asp Tyr Trp Asn Asp Asn Ser Glu

1350
TGC TAC AAT CCA TGT TTC TAT GTA GAA TTA ATT AGA GGA AGG CCT GAA GAA GCA
Cys Tyr Asn Pro Cys Phe Tyr Val Glu Leu Ile Arg Gly Arg Pro Glu Glu Ala

1400
AAA TAT GTT GAA TGG ACC AGT AAC AGC CTA ATT GCA CTA TGT GGG AGC CCA ATC
Lys Tyr Val Glu Trp Thr Ser Asn Ser Leu Ile Ala Leu Cys Gly Ser Pro Ile

1450
TCA GTT GGG TCT GGA TCT TTC CCT GAT GGG GCA CAA ATT AAA TAC TTT TCG TAA
Ser Val Gly Ser Gly Ser Phe Pro Asp Gly Ala Gln Ile Lys Tyr Phe Ser  .
```

FIG. 3-2

1515
aacgaa aaaaaccctt gtttctactc ccccccccc cccccctgcag

FIG. 3-3

EI - A2 neuraminidase (N8)

```
                                                            50
ctgcagggggg gggggagcag gagtttaaa ATG AAT CCA AAT CAA AAG ATA ATA GCA ATT
                                MET Asn Pro Asn Gln Lys Ile Ile Ala Ile 100
GGA TCT GCA TCA TTA GGA ATA CTA ATC CTC AAC GTC ATT CTC CAT GTA GTC AGC
Gly Ser Ala Ser Leu Gly Ile Leu Ile Leu Asn Val Ile Leu His Val Val Ser 150
ATT ATA GTA ACA GTA CTG GTC CTC AAT AAC AAT GGA ACA GGT CTG AAC TGC AAC
Ile Ile Val Thr Val Leu Val Leu Asn Asn Asn Gly Thr Gly Leu Asn Cys Asn 200
GGG ACG ATC ATA AGA GAG TAC AAT GAA ACA GTA AGA GTA GAA AGA ATT ACT CAA
Gly Thr Ile Ile Arg Glu Tyr Asn Glu Thr Val Arg Val Glu Arg Ile Thr Gln 250
TGG TAT AAT ACT AAT ACA ATC GAG TAT ATA GAG AGA CCT TCA AAT GAA TAC TAC
Trp Tyr Asn Thr Asn Thr Ile Glu Tyr Ile Glu Arg Pro Ser Asn Glu Tyr Tyr 300
ATG AAC AAC ACC GAA CCA CTG TGT GAG GCC CAG GGC TTT GCA CCA TTT TCC AAA
MET Asn Asn Thr Glu Pro Leu Cys Glu Ala Gln Gly Phe Ala Pro Phe Ser Lys 350
GAT AAT GGA ATA CGA ATT GGG TCG AGA GGT CAT GTT TTT GTA ATA AGA GAA CCT
Asp Asn Gly Ile Arg Ile Gly Ser Arg Gly His Val Phe Val Ile Arg Glu Pro 400
TTT GTC TCA TGT TCG CCC TTA GAA TGT AGA ACC TTT TTC CTC ACA CAG GGC TCA
Phe Val Ser Cys Ser Pro Leu Glu Cys Arg Thr Phe Phe Leu Thr Gln Gly Ser 450
TTA CTT AAT GAC AAA CAT TCT AAC GGC ACA GTG AAG GAC CGA AGT CCA TAT AGG
Leu Leu Asn Asp Lys His Ser Asn Gly Thr Val Lys Asp Arg Ser Pro Tyr Arg 500
ACT TTG ATG AGT GTC AAA GTA GGG CAA TCA CCT AAT GTG TAT CAA GCT AGG TTT
Thr Leu MET Ser Val Lys Val Gly Gln Ser Pro Asn Val Tyr Gln Ala Arg Phe 550
GAA TCG GTG GCA TGG TCA GCA ACA GCA TGC CAC GAT GGG AAA AAG TGG ATG ACA
Glu Ser Val Ala Trp Ser Ala Thr Ala Cys His Asp Gly Lys Lys Trp MET Thr 600                                                       650
 GTT GGA GTC ACA GGG CCC GAT AAT CAA GCA GTT GCA GTA GTG AAC TAT GGA GGT
 Val Gly Val Thr Gly Pro Asp Asn Gln Ala Val Ala Val Val Asn Tyr Gly Gly 700
GTT CCG GTT GAT ATC ATT AAT TCA TGG GCA GGG GAT ATC CTA AGA ACC CAA GAA
Val Pro Val Asp Ile Ile Asn Ser Trp Ala Gly Asp Ile Leu Arg Thr Gln Glu
```

FIG. 4-1

```
                                                    750
TCG TCA TGC ACC TGC ATT AAA GGA GAC TGT TAT TGG GTG ATG ACT GAT GGA CCG
Ser Ser Cys Thr Cys Ile Lys Gly Asp Cys Tyr Trp Val MET Thr Asp Gly Pro

800
GCA AAC AGG CAA GCT AAA TAT AGG ATA TTC AAA GCA AAA GAT GGA AGA ATA ATT
Ala Asn Arg Gln Ala Lys Tyr Arg Ile Phe Lys Ala Lys Asp Gly Arg Ile Ile

850
GGG CAG ACT GAT ATA AGT TTC AAT GGG GGA CAC ATA GAG GAG TGT TCT TGT TAC
Gly Gln Thr Asp Ile Ser Phe Asn Gly Gly His Ile Glu Glu Cys Ser Cys Tyr

900
CCC AAT GAA GGG AAG GTG GAG TGT GTA TGC AGG GAC AAC TGG ACT GGA ACA AAT
Pro Asn Glu Gly Lys Val Glu Cys Val Cys Arg Asp Asn Trp Thr Gly Thr Asn

950
AGA CCA ATT CTG GTA ATA TCT CCT GAT CTA TCG TAC ACA GTC GGA TAT TTG TGT
Arg Pro Ile Leu Val Ile Ser Pro Asp Leu Ser Tyr Thr Val Gly Tyr Leu Cys

1000
GCT GGC ATT CCC ACT GAC ACT CCT AGG GGA GAG GAT AGT CAA TTC ACA GGC TCA
Ala Gly Ile Pro Thr Asp Thr Pro Arg Gly Glu Asp Ser Gln Phe Thr Gly Ser

1050
TGC ACA AGC CCT TTG GGA AAT AAA GGA TAC GGT GTA AAG GGC TTC GGG TTT CGA
Cys Thr Ser Pro Leu Gly Asn Lys Gly Tyr Gly Val Lys Gly Phe Gly Phe Arg

1100
CAA GGA AAT GAC GTA TGG GCC GGA AGG ACA ATT AGT AGG ACT TCG AGA TCA GGA
Gln Gly Asn Asp Val Trp Ala Gly Arg Thr Ile Ser Arg Thr Ser Arg Ser Gly

1150
TTC GAA ATA ATA AAA ATC AGG AAT GGT TGG ACA CAG AAC AGT AAA GAC CAA ATC
Phe Glu Ile Ile Lys Ile Arg Asn Gly Trp Thr Gln Asn Ser Lys Asp Gln Ile

1200
AGA AAG CAA GTG ATT ATT GAT AAC CTA AAT TGG TCA GGA TAT AGC GGT TCT TTC
Arg Lys Gln Val Ile Ile Asp Asn Leu Asn Trp Ser Gly Tyr Ser Gly Ser Phe 1250                                                              1300
ACA TTG CCG GTT GAA CTA ACA AAA AAA GGA TGT TTA GTC CCC TGT TTC TGG GTT
Thr Leu Pro Val Glu Leu Thr Lys Lys Gly Cys Leu Val Pro Cys Phe Trp Val

1350
GAA ATG ATC AGA GGT AAA CCT GAA GAC ACA ACA ATA TGG ACC TCT AGC AGC TCC
Glu MET Ile Arg Gly Lys Pro Glu Asp Thr Thr Ile Trp Thr Ser Ser Ser Ser

1400
ATT GTG ATG TGT GGA GTA GAC CAT AAA ATT GCC AGT TGG TCA TGG CAC GAT GGA
Ile Val MET Cys Gly Val Asp His Lys Ile Ala Ser Trp Ser Trp His Asp Gly

1450
GCT ATT CTT CCC TTT GAC ATC GAT AAG ATG TAA tttacgaa aaaaaaaaac cccccccccc
Ala Ile Leu Pro Phe Asp Ile Asp Lys MET  .
```

FIG. 4-2

1481
cccccctgcag

FIG. 4-3

METHOD AND COMPOSITIONS USEFUL IN PREVENTING EQUINE INFLUENZA

CROSS-REFERENCE TO RELATED APPLICATION

This application is a continuation-in-part of U.S. patent application Ser. No. 747,020, filed 20 June 1985 now allowed U.S. Pat. No. 4,361,191.

TECHNICAL FIELD

The invention relates to immunizing horses against infection by influenza virus. More particularly, the invention relates to use of vaccinia-carried immunogens and synthetic peptide vaccines useful for this purpose.

BACKGROUND ART

Equine influenza is a highly contagious respiratory infection engendered in horses by equine influenza virus (EIV). While the disease has low mortality, the economic impact is often great due to deterioration of the subject's performance (Mumford, J. A., et al, *Equine Vet J* (1980) 12: 3-9). Current immunization techniques use inactivated or killed EIV. These procedures are characterized by undesirable side effects, and the immunity conferred appears in some cases to last for no more than three or four months. In short, there is no entirely satisfactory vaccine available to prevent the spread of this disease.

Two different serotypes, which are members of the influenza A myxovirus group, have been identified as causative agents of this disease: A/equine/Prague/1/56 (Sovinova, O., et al, *Acta Virol* (English ed.) (1958) 2: 52-61) (designated herein EVI-A1) and A/equine/Miami/1/63 (Waddell, G. H., et al, *J Am Vet Med Assoc* (1963) 143: 587-590) (designated herein EIV-A2). These strains share the characteristics associated with influenza viruses in general, including those viruses responsible for human influenza. Most importantly, the immunological characteristics of influenza virions appear to reside primarily in two virally encoded glycoproteins, the hemagglutinin protein (HA) and the neuraminidase protein (NA), both of which are embedded in the membranous envelope which comprises the outer layer of the virus. These proteins attach themselves to the outer membrane of infected cells. Twelve subtypes of HA (H1-H12) and nine subtypes of NA (N1-N9) have been defined using serological cross-reactivity. Thus, all influenza virus isolates carry a parenthetical description (HxNy) corresponding to the subclasses carried. The two equine strains are designated H7N7 (for EIV-A1) and H3N8 (for EIV-A2). (The designation H3 now is used to include both human H3 and former equine HEq2, although these are not identical proteins. H7 is now used to include both avian Hav7 and former HEq1; these, too, are not identical. N7 is former NEq1 and N8 is former NEq2. (Melnick, J., *Prog Med Virol* (1980) 26: 214-232).)

Both HA and NA are involved in the disease process. HA functions in attachment to host membrane and penetration into the host's cells; immunization in subject experimental animals with HA alone elicits neutralizing antibodies and protection from the disease. NA functions in cell-to-cell transmission, and antisera raised against NA attenuate the disease and decrease the spread of the disease from cell to cell. (Schulman, J. L., in *The Influenza Viruses and Influenza* (1975), E. D. Kilbourne, ed, New York/London: Academic Press, pp. 373-393.)

Human influenza virus and the design of vaccines to protect against it have received considerable attention. Synthetic peptides designed to correspond to a putative antigenic epitope on human HA glycoproteins have been attached to carrier proteins and used to immunize mice against infection with the human influenza virus of the same strain (U.S. Pat. No. 4,474,757). The peptides synthesized were apparently designed based on the sequence of fragments generated by CNBr digestion of the hemagglutinin protein. Synthetic peptide-carrier vaccines have also been suggested as a general approach to protection against viral infection (Brown, F., *Ann Rev Microbiol* (1984) 3: 221-235).

An alternative approach to vaccine compositions which has been suggested recently utilizes the vaccinia virus as a carrier. Mackett, M., et al, *J. Virol* (1984) 49: 857-864 describes this general method. Breifly, vaccinia is a large (187 kb) double-stranded DNA virus which replicates in the cytoplasm of infected cells. It is noninfectious when deproteinized, as it carries its own enzymes for transcription and cannot utilize the machinery of the host cell for this purpose. Vaccinia virus per se was used as the original smallpox vaccine, and is highly desirable as a vaccine carrier because of its low cost and ease of propagation. Freeze-dried vaccinia virus used against smallpox could be mass produced for as little as two cents per dose, while other subunit vaccines, for example, those against hepatitis B, cost approximately $100 per course of immunization. There are other advantages as well. Vaccinia stimulates both the humoral antibody and cell-mediated immunity systems of the subject. The freeze-dried vaccine is stable without refrigeration and is generally potent after a single inoculation. It is also easy to administer under nonsterile field conditions (Smith, G. L., et al, *Biotechniques* (1984) November/December: 306-312). Because of these advantages, vaccinia has been used as a carrier for antigenic proteins of hepatitis B and herpes simplex (Paoletti, E., et al, *Proc Natl Acad Sci* (USA) (1984) 81: 193-197), rabies (Wiktor, T. J., et al, *Proc Natl Acad Sci* (USA) (1984) 81: 7194-7198), and human influenza hemagglutinin (Panicali, D., et al, *Proc Natl Acad Sci* (1983) 80: 5364-5368; Smith, G. L., et al, *Proc Natl Acad Sci* (1983), 80: 7155-7159).

One reason these techniques have not been extensible to equine influenza is the absence of sufficient information on the HA and NA proteins of these viruses. This deficiency is remedied by the present invention, which provides complete genomic and amino acid sequences for the four relevant surface proteins characterizing EIV. In addition, the invention provides properly designed vectors and peptides based on these sequences useful in vaccine compositions.

DISCLOSURE OF THE INVENTION

The invention provides complete genetic sequences encoding the four glycoproteins which characterize the two identified serotypes of EIV. The invention further provides vaccine compositions which are grounded in this genetic information. One class of vaccine compositions comprises modified vaccinia engineered to express the HA and NA surface glycoproteins of the equine infective agents. Another class of compositions comprises synthetic peptide sequences designed to correspond to the antigenic determinants of the HA proteins. These synthetic peptides can be size enhanced, such as by linkage to carrier proteins, to engender an immune response. Still another class comprises the HA or NA proteins per se, which are preferably produced recombinantly in host cells which permit correct post-translational processing. The vaccine compositions of the invention may be used in appropriate protocols for protection of horses against the disease, either in independent vaccine regimes, or as adjuncts to more traditional immunizations using killed virus vaccines. A variety of protocols are workable, and several optimal methods based on these protocols form a part of the invention.

The genetic information contained in the cloned cDNAs representing the EIV glycoproteins is useful in two other ways—to construct diagnostic probes for detection of the disease and to construct probes to obtain new cDNAs associated with mutated forms of the virus.

Thus, in one aspect the invention is directed to recombinant DNA comprising the sequences encoding equine H7, equine H3, equine N7, and equine N8. These recombinant sequences or substantial portions thereof are useful as diagnostic probes for detecting the presence of the disease and as probes to retrieve corresponding cDNA in mutated forms of the virus. These sequences or immunologically effective portions thereof are useful in preparing vaccines against EIV which are constructed by inserting them into nonessential portions of the vaccinia virus genome. Accordingly, in another aspect, the invention relates to the resulting vaccinia-borne compositions. In still another aspect, the invention relates to specific synthetic peptide sequences useful in preparing vaccines effective against EIV. The latter vaccines are prepared either by using these peptides per se or by polymerizing these synthetic sequences or attaching them to carrier proteins to provide enhanced size for immunogenicity. The resulting vaccines also form an aspect of the invention. In still another aspect, the invention relates to vaccines comprised of the HA and/or NA proteins per se. In addition, the invention includes methods to immunize horses against EIV infection by administration of the foregoing compositions, and to prepare vaccines against mutated forms of the virus.

BRIEF DESCRIPTION OF THE DRAWINGS

FIGS. 1-4 show the coding sequences and deduced amino-acid sequences representing the genes and proteins corresponding to H7 (EIV-A1), H3 (EIV-A2), N7 (EIV-A1), and N8 (EIV-A2), respectively.

MODES OF CARRYING OUT THE INVENTION

Figure 5:
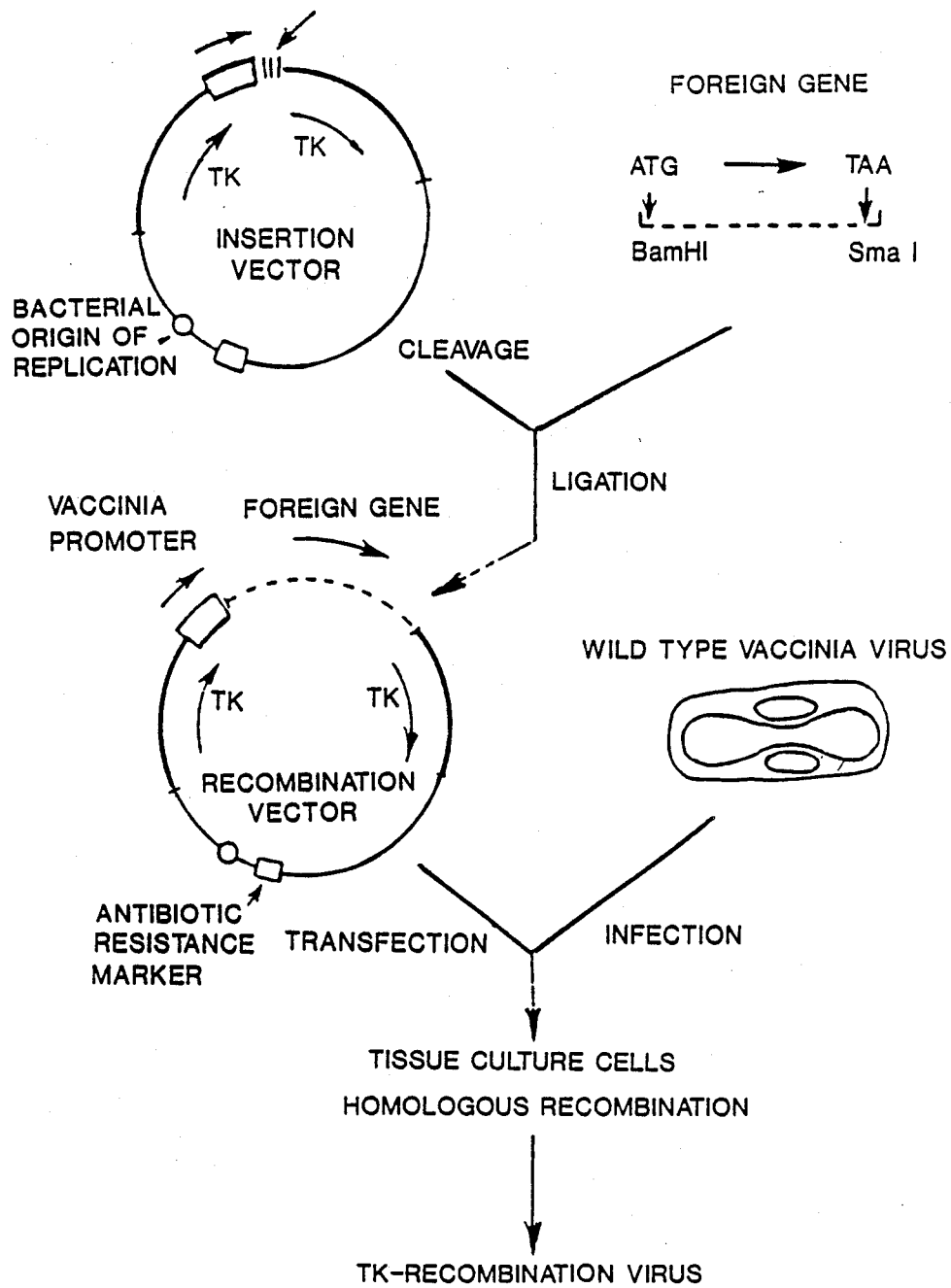
FIG. 5 shows the general method to prepare recombinant vaccinia capable of expressing the EIV derived genes.

A. Definitions and Description of Surface Viral Proteins

Hemagglutinin (HA) in general is a glycoprotein of molecular weight approximately 77 kD, and can be cleaved by protease action and subsequent reduction of the single disulfide bond into an amino terminal HA1 50 kD portion and the carboxy terminal HA2 27 kD portion. Complete nucleotide sequences have been determined for at least four avian and human subtypes: H1, H2, H3, and H7. The primary amino acid sequences of all these HA proteins contain highly conserved crysteine, proline, and glycine residues and glycosylation sites.

Crystallographic studies show that human H3 contains a globular head which extends away from the cellular membrane composed almost entirely of residues of HA1, and an anchoring stalk portion which is comprised of mostly HA2 (Wilson, et al, *Nature* (1981) 289: 366-373). This is believed to be representative for all HA molecules. Four major antigenic sites, all located in the HA1 globular portion, have been identified from less conserved sequences in immunological variants (Wiley, et al, *Nature* (1981) 289: 373-378). As will be seen below, the amino acid sequence of the equine HA polypeptides differs from those previously determined for the forms infective in humans, particularly in the area of the antigenic sites. In addition, HA peptides in general appear to be subject to antigenic drift with time, although the HA protein from EIV-A1 appears relatively stable.

Neuraminidase (NA) is an approximately 56 kD glycoprotein which occurs as a tetramer on the surface of infected cells. Unlike HA, the membrane anchor is at the amino terminus, and the reactive antigenic sites are predominantly in the carboxy terminal two-thirds of the peptide. Comparison of amino acid sequences from representative N1 and N2 human infective serotypes show extensive homology in the antigenic portion of the molecule, but little in the stalk portion. A similar relationship exists between the EIV sequences shown below.

The equine HA and NA DNA, cDNA and polypeptide sequences described below and in the figures are representative of their respective equine subtypes. It is recognized that minor mutational changes may occur without destroying the functionality of the DNA or cDNA sequences in their function as vaccines per se in their function as diagnostic probes, or that of the proteins generated by them. It is not intended that equine H3, equine H7, equine N7, and equine N8 be limited to the precise nucleotide and amino acid sequences shown. To fall within the designations, a particular sequence must only be functionally substantially equivalent to those depicted in the figures.

One obvious source of variation which has minimal effect on functionality as a coding sequence residues in the redundancy of the genetic code. Of course, the designations are intended to include variations in the sequence which result from this codon redundancy. In addition, minor modifications of the amino acid sequence, and thus the coding sequence, may be permitted which still result in proteins capable of the immunological effect desired. Such changes may include deletion, addition, or alteration of a limited number of amino acids. In particular, for use as a probe, only a substantial portion, and not all of the DNA sequence, is required to be effective. Similarly, for use in a vaccinia-borne vaccine, only an "immunologically effective" portion—i.e., sufficient to generate a protein capable of raising neutralizing antibodies—is required. So long as the altered amino acid sequence functions immunologically in the same fashion as the corresponding sequence depicted, it is included in the designation.

It should be understood that "derived from", when referring to a DNA sequence or amino acid sequence, indicates a correspondence in composition to the referenced material, and not necessarily actual physical derivation therefrom. For example, a DNA encoding a signal sequence which is derived from influenza hemagglutinin refers to a DNA constructed so as to encode a peptide sequence substantially similar to that which is found in influenza HA, and that DNA sequence may be constructed by, for example, obtaining cDNA from the mRNA encoding the protein, by synthetic methods using automated oligonucleotide synthesis, or in any other manner designed to recreate a coding sequence for the desired peptide.

B. General Method

Based on the genomic information provided by the invention, three general approaches to preparing vaccines are used: in one, partial or full-length HA and NA cDNA clones are recombined into a nonessential region of vaccinia virus, which then express the inserted EIV antigen coding sequences. These vaccinia serve as complete EIV vaccines. In a second approach, synthetic peptides designed from deduced amino acid sequences of equine HA, if necessary made immunogenic by size enhancement, are used to prepare vaccines. These vaccines are used to boost the protective immune response from animals previously given a single dose of killed whole virus vaccine. Alternatively, the synthetic peptide vaccines may be given as a primer prior to the inoculation with whole virus. In a third approach, full-length, properly processed HA or NA proteins are used as vaccines.

HA and NA are used as the basis for active components of the claimed vaccines because in the case of humans, it is believed that immunity is conferred by response to these corresponding surface proteins (Couch, R. B., et al, *Ann Rev Microbiol* (1983) 527–549). In addition, in horses, antisera raised against whole EIV show high titers of antibody specific against HA of the same serotype strain.

B.1. Cloning and Sequencing of the EIV Genes

It is known that the genomes of influenza virus consist of eight segments of single-stranded RNA, each of which encodes a particular viral protein. The eight segments of RNA from each EIV strain were separated by electrophoresis, and the RNA which encodes HA and that which encodes NA were isolated. cDNA libraries prepared from total viral RNA by conventional methods were screened using reverse transcripts of these RNA isolates and influenza-specific synthetic oligonucleotides as probes. The cDNA clones thus obtained are useful in future preparation of corresponding cDNA for use in vaccines from EIV isolates which have been altered by genetic drift. They thus provide initial probes which enable the production of a series of vaccines corresponding to the inevitable evolutionary drift of the virus.

The positively hybridizing cDNA clones were then sequenced and their identity as HA and NA genes was confirmed by the similarity of the deduced amino acid sequence to known HA and NA proteins. The deduced amino acid sequences were analyzed for antigen sites using secondary structure computer profiles, and by localizing sites known to be important in the disease process, e.g., receptor binding sites.

The resulting cDNAs encoding HA and NA are useful as diagnostic probes for the detection of influenza in horses, as well as in formulating vaccinia-borne vaccines. The probes are used to detect the EIV genome in biological samples such as blood or urine by their ability to hybridize to the target polynucleotide under stringent conditions.

B.2. Generation of Recombinant EIV-Vaccinia Viruses

Figure 6:
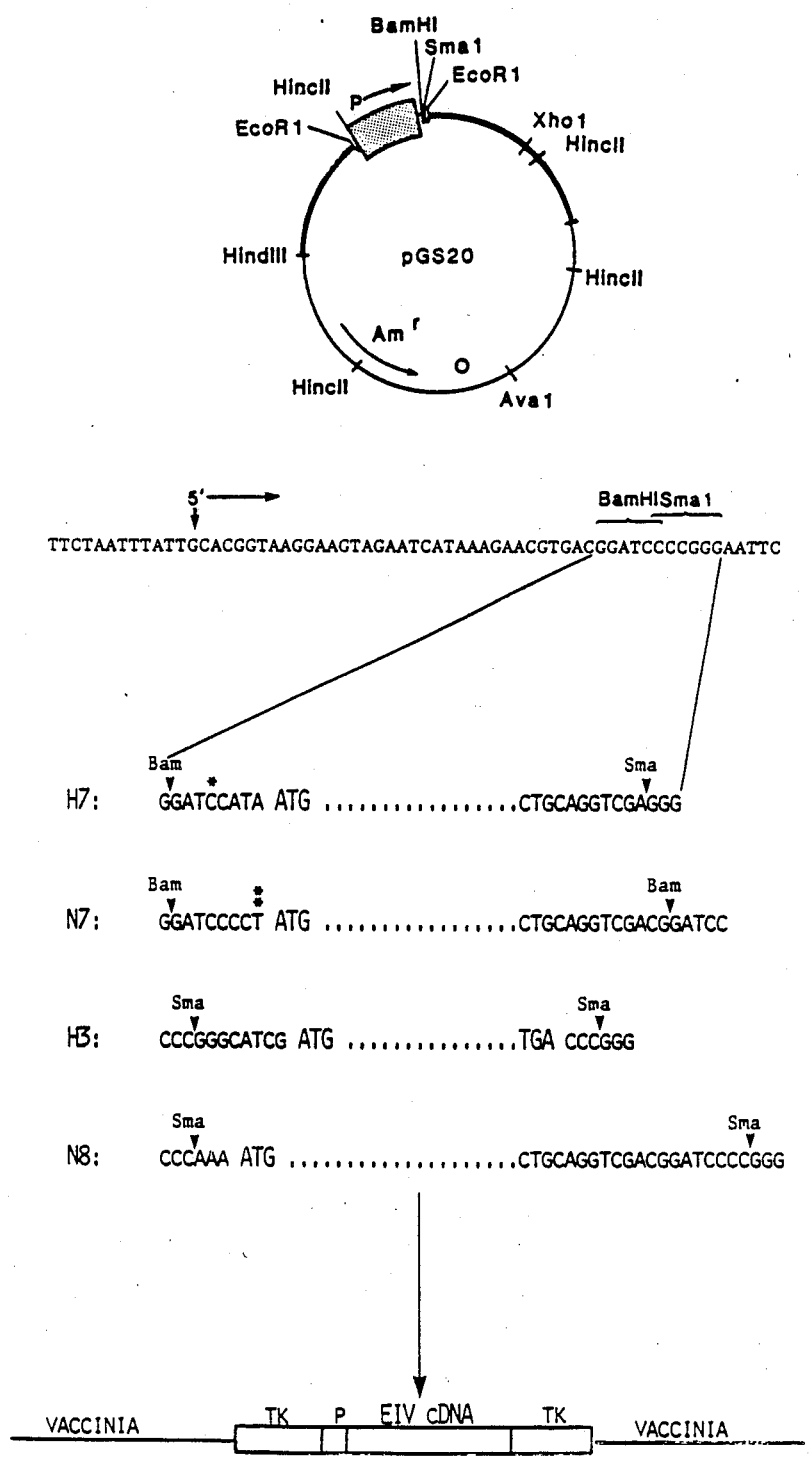
FIG. 6 shows the construction of vectors for preparing recombinant vaccinia bearing the coding sequences of FIGS. 1-4.

The parameters for effecting the integration of foreign DNA into vaccinia are known in the art and are currently in a position for practical utilization. Briefly, the desired immunogen is transferred into a nonessential portion of the vaccinia genome by coinfecting host cells with both native vaccinia and a carrier plasmid which contains the foreign gene sandwiched between sequences homologous with the selected nonessential portion of the vaccinia genome. In addition, the foreign gene is provided with a vaccinia promoter, which will permit its expression under the influence of the vaccinia transcription and translation systems. A general purpose vector capable of housing the foreign gene has been disclosed by Moss, B., et al (*Proc Natl Acad Sci* (USA) (1983) 80: 7155–7159). A diagram of this vector. pGS20, and its manner of use to obtain a recombinant vaccinia virus containing a desired foreign gene is shown in FIG. 5.

pGS20 has a vector fragment derived from pBR328, a vector compatible with *E. coli* which contains the *E. coli* origin of replication and the ampicillin resistance gene. The vector contains the promoter from the 7.5 k gene of vaccinia (a gene encoding a 7500 dalton protein), excised as a 275 bp HincII/RsaI fragment (Venkatsen, et al, *Cell* (1981) 25: 805–813), which is translocated into the EcoRI site of the vaccinia thymidine kinase (TK) gene. Other restriction site modifications have been made for convenience, and there are BamHI and SmaI restriction sites immediately downstream of the promoter to permit foreign gene cloning (Mackett, M., et al, supra, incorporated herein by reference). FIG. 6 shows the nucleotide sequence in the region of the promoter/restriction site fragment junction.

In preparing the vectors of the invention, the DNA encoding the desired immunogen is inserted into pGS20 using the restriction sites downstream of the promoter. In the present invention this DNA is derived from equine H7, H3, N7, or N8 and comprises an immunologically effective portion thereof. The recombination vector is amplified in *E. coli* using transformation to Amp ® and then coinfected along with wild-type vaccinia into CV-1 cells. Unlike other large DNA animal viruses, vaccinia transcribes and replicates its genome in the cytoplasm of infected cells. Many of the enzymes involved in its nucleic acid metabolism, such as DNA and RNA polymerases, enzymes to cap, methylate, and polyadenylate RNA, as well as thymidine kinase, are encoded in its own genome. Indeed, protein-free vaccinia is noninfective—since it encodes its own transcriptase and apparently cannot use the transcriptase used by its eucaryotic host, it cannot synthesize required proteins using its DNA alone in combination with the host cell machinery. Cells having been transformed with both the recombinant, for example pGS20-derived, vector and vaccinia virus mediate recombination of the DNA portion contained within the vaccinia-corresponding segments of the vector into the vaccinia genome. Use of the TK-encoding sequences to effect recombination is particularly desirable, as not only is this a nonessential portion of the vaccinia genome, but a selectable marker is provided for cells containing the recombined vaccinia—i.e., when the foreign DNA is inserted, the TK gene is inactivated, and the tk-recombinant viruses can be selected by plaque assay on tkcells in the presence of 5-bromodeoxyuridine (BUdR). As shown in FIG. 5, tk-recombinant virus plaques can be selected yielding the desired recombinant vaccinia. Additionally, tk-vaccinia have been shown to be $10^5$ to $10^6$ times less virulent in animals as compared to wild-type vaccinia, indicating the potential for an increased safety factor in humans (Smith, G. L., and Moss, B., *Biotechniques* (1984) 306–312).

While pGS20 is a convenient illustrative vector, it is understood that alternative constructions involving other vaccinia promoters in other nonessential regions of the gene may be used (Moss, et al, *Gene Amplification Analysis*, Vol. III, Pappas, T. K., et al, eds. (1982) New York, Elsevier, pp. 201–213; Mackett, M., et al, supra). Not only CV-1, but any competent cells susceptible to vaccinia infection can be used to effect the recombination.

B.3. Preparation of Synthetic Peptides

Peptides were identified as representing antigenic regions of the HA viral proteins by analogy to the corresponding regions in the human influenza proteins, by analysis of the predicted secondary structure of the equine proteins, and by location of key functional areas in the equine proteins. These potential antigenic determinants were synthesized using the solid-state Merrifield method. As these peptides are often too small to be immunogenic, their size is enhanced either by polymerization or by conjugation to a carrier protein.

A variety of techniques is available in the art for such polymerization or conjugation. The most commonly used polymerization technique employs glutaraldehyde and effects self-condensation of the peptide. However, conjugation to a carrier protein is, generally, a preferred approach. Such conjugation is effected by linking agents which attach to each member of the conjugate. For example, there are a large number of hetero bifunctional agents which generate a disulfide link with one component and a peptide link with the other. These have been extensively used. Any of the synthetic peptides disclosed herein may be prepared with an additional cysteine to permit this mode of linkage. The most popular such linking agent is N-succinidyl-3-(2-pyridylthio) propionate (SPDP). Other such agents, which create a disulfide linkage at one end and an amide linkage through an $\epsilon$ amino on a lysine at the other end, are available. See, for example, *Immun Rev* (1982) 82: 185. Still other bifunctional coupling agents form a thioether rather than a disulfide linkage. Many of these thioether-forming agents are commercially available, and include reactive esters of 6-maleimidocaproic acid, 2-bromoacetic acid, 2-iodoacetic acid, and the like. Carboxyl groups of these acids can be activated by combining them with succinimide or 1-hydroxy-2-nitro-4-sulfonic acid, sodium salt. In addition, reagents which operate through dehydration, such as dicyclohexylcarbodiimide, can be used.

B.4. Preparation of Recombinant HA or NA Vaccines

In addition to the vaccines prepared by obtaining recombinant vaccinia virus and by size enhancement of synthetic peptides, larger proteins derived from the HA or NA proteins of the equine influenza viral coat proteins can be prepared. As the entire genome encoding these proteins is available, suitable DNA encoding these proteins in their entirety or such smaller portions thereof which are immunologically effective may be excised from cDNA and ligated into expression vectors for production of these proteins in foreign hosts. While it is conceivable that bacterial hosts can be used, the production of these proteins in mammalian cells lines, or even yeast cells, is preferred, since post-translational processing available in these hosts more accurately simulates that ordinarily carried out in cells infected with the virus. Therefore the recombinant proteins produced would be expected to more closely mimic the viral proteins as ordinarily found by a target cell.

Suitable host mammalian and yeast cells, and appropriate control sequences and transfer vectors effective in such hosts, are found in C.5 below. In general, the desired portion of the protein-encoding DNA sequence is excised from the gene using suitable restriction enzymes, and modified, if necessary, prior to ligating into transfer vectors providing operable control sequences. The ligated vectors are then transformed into the corresponding hosts, and the hosts cultured under conditions known to foster the multiplication of the host cell, and, usually, followed by inducing conditions to activate the control sequences provided. The recombinant HA and NA proteins are then retrieved from the cells, by lysis, if necessary, and purified using standard techniques to obtain the pure recombinant protein.

In addition, the desired recombinant protein may be produced in cell culture using coinfection with vaccinia virus along with the appropriate recombinant pGS20 derivative (Cochran, et al. *Proc Natl Acad Sci* (USA) (1985) 82: 19–23).

B.5. Vaccine Preparation

The vaccines of the invention which are recombined vaccinia virus are employed in the conventional manner. Vaccinia virus can be cultured in standard media, as described below, or by infecting live animals and harvesting the virus from the lesions. The administration of the vaccinia is generally by means of scratching the skin, and non-sterile conditions are often acceptable.

For vaccines which contain peptides or proteins as active ingredients, administration is slightly more complex. Typically, such vaccines are prepared as injectables, either as liquid solutions or suspensions; solid forms suitable for solution in, or suspension, in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other modes of administration include suppositories, intranasal aerosols, and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of manitol, lactose, starch, magnesium stearate, sodium saccharin, cellulose, magnesium carbonate, and the like. These compositions take the form of solutions, suspensions, tablets, pills, capsules, sustained release formulations, or powders, and contain 10%-95% of active ingredient, preferably 25%-70%.

The peptides' proteins may be formulated into the vaccine as neutral or salt forms. Pharmaceutically acceptable salts include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups may be derived from from inorganic bases such as, for example, sodium, potassium, ammonium, calcium, or ferric hydroxides, and such organic bases as isopropylamine, trimethylamine, 2-ethylamino ethanol, histidine, procaine, and the like.

The peptide or protein-based vaccines are administered in a manner compatible with the dosage formulation, and in such amount as will be therapeutically effective an immunogenic. The quantity to be administered depends on the subject horse to be treated, capacity of the subject's immune system to synthesize antibodies, and the degree of protection desired. Precise amounts of active ingredient required to be administered depend on the judgment of the practitioner and are peculiar to each subject. However, suitable dosage ranges are of the order of several hundred micrograms active ingredient per subject. Suitable regimes for initial administration and booster shots are also variable, but are typified by an initial administration followed in one or two week intervals by a subsequent injection or other administration. Alternatively, primer doses of the vaccines of the invention may be used one to two weeks before injection with conventional killed virus vaccine.

Administration is typically by injection intramuscularly, but the peptides or proteins may also be formulated for intranasal application.

A preferred use of the synthetic peptide immunogens is that they be incorporated into existing immunization regimens as either a first or "priming" inoculation or as second and subsequent "boosting" inoculations in combination with other vaccines. It has been shown by others that a single dose of a synthetic peptide "primes" the immune system such that subsequent inoculation with the whole virus (e.g., poliovirus) elicits extremely high titers of neutralizing antibodies. The practice of priming or boosting with synthetic peptides offers two major advantages: it lessens the number of whole virus vaccine inoculations (and the accompanying side effects) required to achieve immunity, and it retains at least one dose of whole virus vaccine in the immunization regimen, thus allowing the animal's immune system an opportunity to see the entire antigenic repertoire of the pathogen.

C. Standard Methods

C.1. Preparation of cDNA

First-strand cDNA was synthesized using RNA-dependent DNA polymerase from avian myeloblastosis virus (AMV), according to Ulrich, A., et al, *Science* (1977) 196: 1313-1319, using an appropriate primer. RNA template was removed by denaturation at 100° C. for five minutes followed by chilling on ice and centrifugation at 5000 rpm for 10 min at room temperature. The supernatant was treated with DNA polymerase I, large fragment to synthesize the second strand. The hairpin loop was cleaved with S1 nuclease from *Aspergillus oryzae* in 300 mM NaCl, 30 mM NaOAc, pH 4.5, 3 mM $ZnCl_2$ for 30 min at 37° C. with 600 units of enzyme. After extraction of cDNA with phenol/chloroform, small oligonucleotides were removed by three ethanol precipitations in the presence of ammonium acetate, i.e., using ½ volume 7.5M ammonium acetate and two volumes of ethanol at −70° C. The resulting blunt-ended, double-stranded cDNA can then be fractionated either using gel filtration through a Sepharose 4B (Pharmacia) or by ultracentrifugation in 5-20% gradients of glycerol in 100 mM NaCl, 10 mM Tris-HCl, pH 7.6, and 1M EDTA, followed by fractionation of the gradient.

The double-stranded DNA was then cloned into suitable vectors using homopolymeric tailing essentially as described by Sutcliffe, J. G., *Nucleic Acid Res* (1978) 5: 2721-2732.

Thus, to complete cDNA libraries in pBR322, double-stranded cDNAs were tailed with dCTP using a reaction containing 0.2M potassium cacodylate, 25 mM Tris, pH 6.9, 2 mM dithiothreitol, 0.5 mM $CoCl_2$, 200 mM dCTP, 400 µ/ml BSA, and 40 units calf thymus terminal transferase for 5 min at 22° C. After extraction with phenol/chloroform and ethanol precipitation the dC-tailed cDNA was annealed with PstI-digested pBR322 tailed with oligo-dG using 2.5 µg pBR322 per 1 µg cDNA/ml. The annealed mixture was transferred into *E. coli* 1061 using the $CaCl_2$ treatment of Casabadan, N., et al, *J Mol Biol* (1980) 138: 179-207.

C.2. Screening cDNA Libraries cDNA libraries were screened by replicating plates onto duplicate nitrocellulose filters (S&S BA-85) and permitting the colonies to grow at 37° C. for 14-16 hr on L-agar containing 15 µg/ml tetracycline, followed by 12-24 hr on L-agar containing 170 µg/ml chloramphenicol. Colonies were lysed with 10% SDS, and the DNA fixed to the filter by sequential treatment for 5 min with 0.5M NaOH, 1.5M NaCl, then 0.5 Tris-HCl, pH 8.0, 1.5M NaCl, followed by 2× standard saline citrate (1× SSC=0.5M NaCl, 0.105M sodium citrate). Filters were air-dried and baked at 80° C. for 2 hr in vacuo.

For nick-translated probe, the duplicate filters are prehybridized at 42° C. for 16-18 hr with 10 ml per filter of DNA hybridization buffer (50% formamide (40% formamide if reduced stringency), 5× SSC, pH 7.0, 5× Denhardt's solution (polyvinylpyrrolidine, plus Ficoll and bovine serum albumin: 1× =0.02% of each), 50 mM sodium phosphate buffer at pH 7.0, 0.2% SDS, 50 µg/ml yeast tRNA, and 50 µg/ml denatured and sheared salmon sperm DNA).

Samples are hybridized with nick-translated DNA probes at 42° C. for 12-36 hr for homologous species and 37° C. for heterologous species contained in 5 ml of this same DNA hybridization buffer. The filters are washed two times for 30 min, each time at 50° C., in 0.2× SSC, 0.1% SDS for homologous species hybridization, and at 50° C. in 3× SSC, 0.1% SDS for heterologous species hybridization. Filters are air dried and autoradiographed for 1-3 days at −70° C.

For synthetic (12-30 mer) oligonucleotide probes, the duplicate filters are prehybridized at 42° C. for 2-8 hr with 10 ml per filter of oligo-hybridization buffer (6× SSC, 0.1% SDS, 1 mM EDTA, 5× Denhardt's, 0.05% sodium pyrophosphate and 50 µg/ml denatured and sheared salmon sperm DNA).

The samples are hybridized with kinased oligonucleotide probes of 12-30 nucleotides under conditions which depend on the composition of the oligonucleotide. Typical conditions employ a temperature of 30°–42° C. for 24–36 hr with 5 ml/filter of this same oligo-hybridization buffer containing probe. The filters are washed two times for 15 min at 23° C., each time with 6× SSC, 0.1% SDS and 50 mM sodium phosphate buffer at pH 7, then are washed once for 2 min at the calculated hybridization temperature with 6× SSC and 0.1% SDS, air dried, and are autoradiographed at −70° C. for 2 to 3 days.

C.3. Vector Construction and Verification

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacylamide gel or agarose gel electrophoresis using standard techniques. A general description of size separations is found in *Methods in Enzymology* (1980) 65: 499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 5–10 μM dNTPs. The Klenow fragment fills in at 5' sticky ends but chews back protuding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Synthetic oligonucleotides are prepared by the method of Efimov,, V. A., et al (*Nucleic Acids Res* (1982) 6875–6894), and can be prepared using commercially available automated oligonucleotide synthesizers. Kinasing of single strands prior to annealing or for labeling is achieved using an excess, e.g.. approximately 10 units of polynucleotide kinase to 1 nmole substrate in the presence of 50 mM Tris, pH 7.6, 10 mM MgCl$_2$, 5 mM dithiothreitol, 1–2 mM ATP, 1.7 pmoles γ32P-ATP (2.9 mCi/mmole), 0.1 mM spermidine, 0.1 mM EDTA.

Ligations are performed in 15–50 μl volumes under the following standard conditions and temperatures: 20 mM Tris-Cl pH 7.5, 10 mM MgCl$_2$, 10 mM DTT, 33 μg/ml BSA, 10 mM–50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of liners) are performed at 1 μM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of Na$^+$ and Mg$^{+2}$ using about 1 unit of BAP or CIP per μg of vector at 60° for about one hour. In order to recover the nucleicd acid fragments, the preparation is extracted with phenol/chloroform and ethanol precipitated. Alternatively. religation can be prevented in vectors which have been double digested by additional restriction enzyme digestion of the unwanted fragments.

Ligations for plasmid construction are confirmed by first transforming *E. coli* strain MC1061 obtained from Dr. M. Casadaban (Casadaban, M., et al. *J Mol Biol* (1980) 138: 179–207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci (USA)* (1969) 62: 1159, optionally following chloramphenicol amplification (Clewell, D. B., *J Bacteriol* (1972) 110: 667). The isolated DNA is analyzed by restriction and/or sequenced by the dideoxy method of Sanger, F., et al, *Proc Natl Acad Sci (USA)* (1977) 74: 5463 as further described by Messing, et al, *Nucleic Acids Res* (1981) 9: 309, or by the method of Maxam, et al, *Methods in Enzymology* (1980) 65: 499.

C.4 Site-Specific Mutagenesis

For portions of vectors derived from cDNA or genomic DNA which require sequence modifications, site specific primer directed mutagenesis is used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form: 50% will have the original sequence. The resulting plaques are hybridized with kinased synthetic primer and then washed at a temperature which permits hybrids of an exact match to remain, but at which the mismatches with the original strand are washed off. Plaques which remain hybridized to the probe at the stringent wash temperature are then picked, cultured, and the DNA recovered.

For probing, plaques are screened by replicating the plaques onto duplicate nitrocellulose filter papers (S&S type BA-85) and infected cells are allowed to grow at 37° C. for 14-16 hr on L agar containing 15 μg/ml tetracycline. The colonies are lysed with 10% SDS and the DNA is fixed to the filter by sequential treatment for 5 min with 500 mM NaOH/1.5M NaCl, then 0.5M Tris HCl (pH 8.0)/1.5M NaCl followed by 2× standard saline citrate (SSC). Filters are air dried and baked at 80° C. for 2 hr.

For synthetic (12-30 mer) oligonucleotide probes, the duplicate filters are prehybridized at 42° C. for 2-8 hr with 10 ml per filter of oligo-hybridization buffer (6× SSC, 0.1% SDS, 1 mM EDTA, 5× Denhardt's, 0.05% sodium pyrophosphate and 50 μg/ml denatured and sheared salmon sperm DNA).

The samples are hybridized with kinased oligonucleotide probes of 12-30 nucleotides under conditions which depend on the composition of the oligonucleotide. Typical conditions employ a temperature of 30°-42° C. for 24-36 hr with 5 ml/filter of this same oligo-hybridization buffer containing probe. The filters are washed two times for 15 min at 23° C., each time with 6× SSC, 0.1% SDS and 50 mM sodium phosphate buffer at pH 7, then are washed once for 2 min at the stringent wash temperature with 6× SSC and 0.1% SDS. Typically, the stringent wash temperature for oligonuceotides of 16-24 bases with from 1 to 3 mismatches will be 40°-70° C., and can most easily be determined by successive washes of the hybridized filter. For example, the hybridized filters can be washed first at 40° C., then at 50° C., then at 60° C., and then at 70° C., with air drying of the filter and autoradiography at −70° C. overnight between each wash.

A shorter modification of this procedure was particularly useful in the construction of mutated sequences containing new restriction sites. In this modification, the sequence to be modified is excised and inserted into M13 vectors as a single strand and the preparation is treated with Klenow in the presence of primer to create a heteroduplex, as in the above conventional procedure. The insert is then removed from the phage vector and cloned into a convenient host plasmid, such as a pUC or pBR plasmid for amplification. After amplification the plasmid DNA is cut with a restriction enzyme protocol which includes the enzyme recognizing the desired new site. Only the mutagenized double-stranded plasmids yield the correct length fragment. These fragments are isolated, for example on gels, and no probing is necessary.

C.5. Hosts and Control Sequences

Both procaryotic and eucaryotic systems may be used to express the EIV encoding sequences; procaryotic hosts are the most convenient for cloning procedures. Procaryotes most frequently are represented by various strains of *E. coli;* however, other microbial strains may also be used. Plasmid vectors which contain replication sites and control sequences derived from a species compatible with the host are used; for example, *E. coli* is typically transformed using derivatives of the pUC series or pBR322. pBR322, for example, contains genes for ampicillin and tetracycline resistance, and thus provides additional markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al, *Nature* (1977) 198: 1056 and the tryptophan (trp) promoter system (Goeddel, et al *Nucleic Acids Res* (1980) 8: 4057 and hybrid control systems such as those employing upstream trp and downstream lac regions.

Eucaryotic hosts are often preferred because of their ability to effect post-translational processing. Microbial eucaryotic hosts include yeast; laboratory strains of *Saccharomyces cerevisiae,* Baker's yeast, are most used although a number of other strains are commonly available. Vectors employing, for example, the 2μ origin of replication of Broach, J. R., *Meth Enz* (1983) 101: 307, or other yeast compatible origins of replications (see, for example, Stinchcomb, et al, *Nature* (1979) 282: 39, Tschempe, et al, *Gene* (1980) 10: 157 and Clarke, L, et al, *Meth Enz* (1983) 101: 300) may be used. Control sequences for yeast vectors include promoters for the synthesis of glycolytic enzymes (Hess, et al, *J Adv Enzyme Reg* (1968) 7: 149; Holland, et al, *Biochemistry* (1978) 17: 4900). Additional promoters known in the art include the promoter for 3-phosphoglycerate kinase (Hitzeman, et al, *J. Biol Chem* (1980) 255: 2073), and those for other glycolytic enzymes.

Eucaryotic host cell cultures derived from multicellular organisms may be used also. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273: 113), or other viral promoters such as those derived from polyoma, Adenovirus 2, bovine papiloma virus, or avian sarcoma viruses. The controllable promoter, hMTII (Karin, M., et al, *Nature* (1982) 299: 797-802) may also be used. General aspects of mammalian cell host system transformations have been described by Axel; U.S. Pat. No. 4,399,216 issued 16 Aug. 1983. It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

Depending on the host cell used, transformation is done using standard techniques appropriate to such cells. The calcium treatment employing calcium chloride, as described by Cohen, S. N., *Proc Natl Acad Sci* (*USA*) (1972) 69: 2110, or the RbCl$_2$ method described in Maniatis, et al, *Molecular Cloning: A Laboratory Manual* (1982) Cold Spring Harbor Press, p. 254 may be used for procaryotes or other cells which contain substantial cell wall barriers. For mammalian cells without such cell walls, the calcium phosphate precipitation method of Graham and van der Eb, *Virology* (1978) 52: 546, optionally as modified by Wigler, M., et al, *Cell* (1979) 16: 777-785 may be used. Transformations into yeast may be carried out according to the method of Van Solingen, P., et al, *J Bact* (1977) 130: 946 or of Hsiao, C. L., et al, *Proc Natl Acad Sci (USA)* (1979) 76: 3829.

C.6. ELISA Assay for Antibodies Against Test Peptides

The synthetic peptides of the invention and their size-enhanced derivatives were used to immunize rabbits and mice, and their ability to raise antibodies in sera was evaluated using an enzyme-linked immunosorbent assay (ELISA). The appropriate peptide for reaction with the antisera was bound to 96-well plates by pretreating the wells in 2% glutaraldehyde for 2 hr at room temperature and then incubating a solution of the appropriate peptide (100 μl of 50 μg peptide/ml PBS) in the wells for 2 hr at 37° C. After washing, the wells received fourfold dilutions of antisera ranging from 1/20 to 1/327,680, and the plates were incubated for 2 hr at 37° C. After washing, the wells received a 1/3500 dilution of horseradish peroxidase-conjugated goat anti-rabbit immunoglobulin (Boehringer-Mannheim) in 0.1% ovalbumin and 0.05% Tween-20 in PBS. The plates were incubated at 4° C. overnight. After washing, a solution of 0.1% citric acid, pH 5.0, 0.04% o-phenyldiamine, and 0.012% peroxide was added to each well, and the plates were incubated for 5–30 min at room temperature. The color reaction was stopped by adding 4N HCl and the absorbance at 490 nm was read on a Biotek ELISA Reader, Model EL-308. Titers for each serum were determined by plotting absorbance against serum dilution for both preimmune and immune samples.

C.7 Plaque Reduction Assay

The ability of antisera to neutralize virus was tested using a plaque reduction assay. Preimmune sera were used as controls. Antisera to be tested and control antisera were heat-treated at 56° C. for 30 min in order to inactivate nonspecific antiviral agents present in all mammalian sera. 100–150 plaque-forming units (pfu) of EIV were incubated with an equal volume of appropriately diluted control and test sera (usually twofold dilutions) for 1 hr at 25° C. Monolayers of MCDK cells were then inoculated with the virus/serum mixture and adsorption allowed to take place for 1 hr at room temperature. The monolayers were then rinsed with Earl's basic salt solution and overlaid with a mixture of DMEM and 0.8% agarose containing 2.5 μg/ml trypsin. The wells were incubated in a 5% $CO_2$ atmosphere at 37° C. for 4 days in order allow plaque formation by viable virus. Cells were stained with crystal violet and total plaques recorded. The serum neutralization titer was determined as the dilution of the serum that reduced EIV pfu by greater than 50%.

D. Examples

The following examples are intended to illustrate the invention, but not to limit its scope.

D.1. Preparation and Sequencing of Equine HA and NA cDNA

Both known EIV strains were used as sources of RNA encoding the desired proteins. Any fresh isolate from a diseased animal can be used as starting material; both EIV-A1 and EIV-A2 are pandemic in the diseased equine population. In the examples below, EIV-A1 stain (H7N7) was originally isolated from an infected horse in Florida in 1973 and passed in four isolation ponies at Cornell University before being propagated in Madin-Darby canine kidney (MDCK) cells. It is designated A1/Cornel/16/74. The EIV-A2 strain (H3N8), designated A2/Kentucky/1/81, was obtained as an allantoic fluid preparation. Both stocks were shown to produce clinically recognizable disease in horses.

These strains, propagated in MDCK cells, were concentrated by centrifugation and purified by banding twice in 30%/60% discontinuous sucrose gradients. The purified virus was treated with 10 μg/ml DNase at 23° C. for twenty minutes, and the virions were disrupted using 0.5% SDS followed by two extractions with phenol:chloroform:isoamyl alcohol (50:50:1) and two extractions with chloroform:isoamyl alcohol (50:1). The aqueous phase was adjusted to 0.3M sodium acetate, and RNA was precipitated with 2½ volumes absolute ethanol.

Preparation of cDNA Probes

To isolate RNA fragments of cDNA probe preparation, 1.5–2 μg viral RNA was denatured in 10 mM methylmercuric hydroxide for 1.5 minutes at 65° C. and then electrophoresed on a 1.4% agarose gel in Tris-borate buffer (0.089M Tris, 0.089M boric acid, 0.02M EDTA) at 12 V/cm for two hours. The gel was stained using 0.5 μg/ml ethidium bromide. The RNA bands identified as HA or NA (by size analogy to human influenza models) were then used to prepare cDNA probes by the method of Lonberg and Gilbert, *Proc Natl Acad Sci* (*USA*) (1983) 80: 3661–3665. Briefly, 5–10 μg agarose plugs were removed from the appropriate areas of the gel with 50 μl capillary tubes and the plugs melted at 65° C. for three minutes and cooled to 37° C. First strand cDNA was obtained using RNA-dependent DNA polymerase, as in section C.1. Calf thymus DNA was used as a random primer.

Preparation of cDNA Libraries Containing HA and NA cDNA libraries in pBR322 were prepared from total RNA of each strain. The cDNA libraries were prepared as described above using two primer methods. In the first method, oligo-dT 12–18 mers were used as primers after addition of poly-A tails to the viral negative stranded poly-A deficient RNA. Three μg of viral RNA was incubated with *E. coli* poly-A plymerase in a reaction containing 50 mM Tris-HCl, pH 7.6, 10 mM $MgCl_2$, 2.5 mM $MnCl_2$, 250 mM NaCl, 10 mM ATP for 3 min at 37° C. and then extracted with phenol/-chloroform and ethanol-precipitated. The resulting extended RNA was used as template.

In the alternative method, the synthetic oligomer 5'-AGCAAAAGCAGG-3' (oligo a), which is a known complement to twelve nucleotides in the 3' terminal untranslated region of each of the eight individual viral RNAs in all influenza viruses was used as primer. A second synthetic primer 5'-AGTAGAAACAAGG-3' (oligo b), which complements an influenza consensus sequence in the 5' untranslated region at the upstream end of each coding region in the viral RNA, was used to prime the complementary strand. Three μg viral RNA yielded approximately 1 μg cDNA size selected to 500 bp; and each library contained about 500,000 independent recombinants.

For probing with cDNA probes, hybridization buffer contained 50% formamide, 5× SSC, 50 mM HEPES, pH 8.0, 5× Denhardt solution (1× Denhardt's = 0.02% each polyvinyl pyrollidine, Ficoll, and BSA), 0.1% SDS, 50 mM/ml yeast tRNA, and 50 mM sheared and denatured salmon sperm DNA. For probing with synthetic probes, the hybridization buffer contained 6× SSC, 0.1% SDS, 1 mM EDTA, 5× Denhardt's, 0.05% sodium pyrophosphate, and 15 µg/ml denatured and sheared salmon sperm DNA.

Isolation of HA and NA cDNA Sequences

The cDNA libraries were probed used one of the reverse-transcribed RNA for each of the desired H7, H3, N7, and N8 sequences prepared as described above and using the two synthetic oligomers used for priming in the reverse-transcribed synthesis, as also described (oligos a and b). For reverse-transcribed RNA, rehybridization was at 42° C. for 12-14 hr, and hybridization was at 42° C. for 12-36 hr using $10^5$ cpm/filter. For probing with oligos a or b, prehybridization was at 42° C. for 2-8 hours and hybridization, at 33° C. for 6-12 hours using $10^6$ cpm/filter kinased probe. (The 33° C. temperature was calculated using the formula $T_H = 4[G+C] + 2[A+T] - 3°$ C. Suggs, S. V., et al, *Developmental Biology Using Purified Genes* (1981), ed. D. D. Brown and C. F. Fox, Academic Press, New York, pp. 683-693.) For the RNA probe, the filters were washed twice for 30 min each at 50° C. in 0.2× SSC, 0.1% SDS, and then air dried and autoradiographed for 1-3 days at −70° C. For the oligo probes the filters were washed twice for 2 min at 23° C. each, with 6× SSC, 0.1% SDS, and 0.05% sodium pyrophosphate, then for 2 min at 33° C. in the same buffer, and then air dired and autoradiographed at −70° C. for 1-2 days. A large number of positive clones were obtained from both EIV-A1 and EIV-A2 libraries, but only one clone from each library which hybridized with all three probes in each of the four cases was retained for further study.

The resulting clones representing H7, H3, N7, and N8 were sequenced by subcloning into M13 mp8, mp9, mp18, and mp19 (Messing, J. et al, *Gene* (1982) 19: 269-276) following sequence determination using the dideoxy method of Sanger, et al, *Proc Natl Acad Sci (USA)* (1977), 74: 5463-5467. The nucleotide sequence of the cDNA sequences for H7, H3, N7, and N8 are shown in FIGS. 1-4.

Examination of the sequences in FIGS. 1-4 indicates the characteristic features of HA1 and HA2 proteins from H7 and H3, including conserved cysteines, clip sites between HA1 and HA2, and the conserved membrane fusion region at the amino terminus of HA2.

D.2. Synthesis of Synthetic Peptides Based HA Sequence Information

The following peptides were synthesized using the method of Merrifield, J., *J. Amer Chem Soc* (1963) 85: 2149–2154.

Based on the EIV-A1 (H7):

(A1-X) representing residues 146–173: Ala-Cys-Arg-Arg-Ser-Arg-Ser-Ser-Phe-Tyr-Ala-Glu-Met-Lys-Trp-Leu-Leu-Ser-Asn-Thr-Asp-Asn-Gly-Val-Phe-Pro-Gln-Met.

(A1-Y) representing residues 181–209: (Cys)-Lys-Arg-Glu-Pro-Ala-Leu-Ile-Ile-Trp-Gly-Ile-His-His-Ser-Gly-Ser-Thr-Ala-Glu-Gln-Thr-Arg-Leu-Tyr-Gly-Ser-Gly-Asn-Lys-(Cys).

(A1-Z) representing residues 309–337: Arg-Ala-Ile-Gly-Lys-Cys-Pro-Arg-Tyr-Val-Lys-Gln-Lys-Ser-Leu-Met-Leu-Ala-Thr-Gly-Met-Lys-Asn-Val-Pro-Glu-Asn-Ser-Thr.

For EIV-A2:

(A2-X) representing residues 143–159: Thr-Gly-Val-Thr-Gln-Asn-Gly-Arg-Ser-Gly-Ala-Cys-Arg-Arg-Gly-Ser-Ala-(Ser)-(Arg).

(A2-Y) representing residues 191–218: Lys-Leu-Tyr-Ile-Trp-Gly-Ile-His-His-Pro-Ser-Thr-Asn-Asn-Glu-Gln-Thr-Lys-Leu-Tyr-Ile-Gln-Glu-Ser-Gly-Arg-Val-Thr.

(A2-Z) representing residues 322–343: Lys-Tyr-Ile-Lys-Gln-Asn-Thr-Leu-Lys-Leu-Ala-Thr-Gly-Met-Arg-Asn-Val-Pro-Glu-Lys-Gln-Ile.

Finally, a synthetic peptide was designed after the amino terminus of the HA2 portion of both the H7 and H3 hemagglutinins (residues 345–357 in H3 and 350–362 in H7):

(A1/A2-N) Gly-Ile-Phe-Gly-Ala-Ile-Ala-Gly-Phe-Ile-Glu-Asn-Gly-(Lys)-(Lys).

Residues in parenthesis are not present in natural sequence but were added for purposes of peptide conjugation or ease in synthesis.

The foregoing peptides are designated by the shorthand symbols shown, and were selected for synthesis on the following basis: both X-peptides (A1-X and A2-X) and Y-peptides (A1-Y and A2-Y) correspond to regions in the human analogs which are major antigenic sites as mapped by monoclonal antibodies and by sequencing of wild-type variants, and thus represent epitopes which, in the human model, elicit B-cell response.

The Y-peptides and Z-peptides (A1-Z and A2-Z) are derived from areas which, in human analogs, have been shown to be recognized by T-cells, and may thus function in those analogs to elicit a T-helper cell response and/or a cytolytic T-cell response (Lamb, J. R., et al, *Nature* (1982) 300: 66–69; Wabuke-Bunoti, M.A.N., et al, *J. Immunol* (1984) 133: 2194–2201). Both Z-peptides and the N-peptide are derived from portions which correspond, in the human hemagglutinin, to areas of antigenic stability.

The foregoing peptides were used to immunize rabbits or mice both as prepared and as modified to enhance presentation size in the injected subject. For size enhancement, peptides were either self-polymerized with glutaraldehyde or covalently linked to keyhole limpet hemocyanin (KLH) using 1-ethyl-3-(3-dimethylaminopropyl)carbodiimide.

For polymerization with glutaraldehyde, 4–10 mg/ml peptide was incubated at 21° C. for 2 hr in 50 mM $NaHPO_4$ (pH 7.5), 150 mM glutaraldehyde. Insoluble products resulted after one or more hours, and the precipitate was resuspended and mixed with Freund's adjuvant for immunization.

For conjugation to KLH, peptide at 4–10 mg/ml was incubated at 4° C. for 20 min in the presence of 1 mg/ml carbodiimide in distilled water, adjusted to pH 3.5 with 1N HCl. KLH was added at 1 mg/ml and the pH of the solution was adjusted to 9.0 with 5 volumes of distilled water containing 1 mM NaOH. The mixture was incubated for 2 hr at 21° C. and dialyzed against phosphate-buffered saline at 4° C. for 16 hr. After dialysis, the conjugated peptides were mixed with Freund's adjuvant for immunization.

D.3. Immunization with Synthetic Peptides Antigenicity

The synthetic peptides were shown to be antigenic in rabbits and mice by ELISA assay of sera obtained from animals injected with each synthetic peptide. The same synthetic peptide was used as the antigen in the ELISA assay of ¶C.6.

For rabbits, each animal received a total of two inoculations. The first inoculation was administered intranodally with complete Freund's adjuvant. The following booster at three weeks was injected intramuscularly with incomplete Freund's adjuvant. The animals received 125 μg of free peptide or polymerized peptide per dose, or 165 μg of KLH peptide conjugate (20 peptide:1 KLH). The animals were bled from the ear vein before the first inoculation to obtain preimmune serum, and ten days after each subsequent inoculation.

For mice, eight-week-old female Balb/C mice received two inoculations of the same preparations as were used for rabbits, except that the peptide content in each dose was 20 μg. The first inoculation was given intramuscularly with complete Freund's adjuvant; the second, three weeks later, in incomplete adjuvant. Animals were bled from the eye seven or eight days after each inoculation.

Table 1 shows the results for the A1-X and A1-Y peptides and their derivatives.

TABLE 1

| | Peptide | Method of Peptide Presentation | Anti-Peptide Antibody Titer |
|---|---|---|---|
| Rabbit 2A1 | A1-X | Free | * |
| Rabbit 2A2 | " | Free | 1/20,480 |
| Rabbit 2B1 | " | Polymerized | 1/80 |
| Rabbit 2B2 | " | Polymerized | 1/80 |
| Rabbit 2C1 | " | Conjugated to KLH | 1/5120 |
| Rabbit 2C2 | " | Conjugated to KLH | 1/5120 |
| Mouse 2fA | A1-X | Free | 1/1280 |
| Mouse 2fB | " | Free | 1/1280 |
| Mouse 2pA | " | Polymerized | 1/320 |
| Mouse 2pB | " | Polymerized | <1/20 |
| Mouse 2cA | " | Conjugated to KLH | 1/81,920 |
| Mouse 2cB | " | Conjugated to KLH | 1/81,920 |
| Mouse 3fA | A1-Y | Free | 1/320 |
| Mouse 3fB | " | Free | <1/20 |
| Mouse 3pA | " | Polymerized | 1/80 |
| Mouse 3pB | " | Polymerized | 1/80 |
| Mouse 3cA | " | Conjugated to KLH | 1/320 |
| Mouse 3cB | " | Conjugated to KLH | 1/320 |

*Animal died.

These data indicate that the synthetic peptides of this invention will elicit moderate to high antibody titers when administered in free and/or size-enhanced form.

Use of the Synthetic Peptides as Immunogenic Boosters

Eight-week-old Balb/C mice received single intramuscular injections of 100 μl of Equicine (Bayvet, Miles Laboratories). Equicine is a killed virus vaccine containing both A1 and A2 EIV serotypes. Three weeks later, the mice received either a second dose of Equicine or a mixture containing 15 μg each of the 7 peptides prepared in ¶D.2 in incomplete Freund's adjuvant. Six days after the second inoculation, the animals were bled from the eye, and the sera were assayed for neutralizing activity against EIV-A1 virus in a plaque reduction assay.

The results are given in Table 4.

TABLE 4

| Animal | Boost | Plaque reduction titer (EIV-A1) |
|---|---|---|
| 10A | Equicine | 1/160 |
| 10B | Equicine | 1/80-1/160 |
| 11A | EIV peps | 1/40 |
| 11B | " | >1/320 |
| 11C | " | >>1/320 |
| 11D | " | 1/20 |
| 11E | " | >1/320 |

TABLE 4-continued

| Animal | Boost | Plaque reduction titer (EIV-A1) |
|---|---|---|
| 11F | " | 1/80 |

The results show that the EIV peptides were as, or more, effective in 4 of 6 animals than additional killed virus in maintaining the level of neutralizing plaque-reduction antibodies. The same results may be achieved when the titer against EIV-A2 virus is analyzed.

A second similar experiment was performed to determine whether EIV synthetic peptides could be used in an adjuvant other than incomplete Freund's to boost neutralizing titer after a single inoculation of Equicine. The adjuvant preparation selected is a form of Halvogen™, an adjuvant used in Equicine vaccine and approved for equine usage. It has the composition 7% Tween 20, 3% Arlacel 20, 50% soybean oil, and 1% Carbopol in $H_2O$.

Five groups of three mice each were inoculated with a 100 μl dose of Equicine. Group I received two boosts of Equicine at three week intervals; Group II received two boosts of 15 μg each peptide (105 μg total) in incomplete Freund's adjuvant (IFA); Group III received two boosts of -μg each peptide in the above Halvogen™ adjuvant; Group IV received two boosts of 15 μg each peptide in aqueous solution (no adjuvant); Group V received no boosts. The mice were bled eight days after the second boost; the sera in each group were pooled, heat treated, and assayed in the plaque reduction assay. The results are presented in Table 5.

TABLE 5

| Group | Boost | Plaque reduction titer (EIV-A1) |
|---|---|---|
| I | Equicine | 1/640 |
| II | EIV peps in IFA | 1/1280 |
| III | EIV peps in Halvogen | 1/640 |
| IV | EIV peps in aqueous (no adjuvant) | 1/320 |
| V | None | 1/160 |

The results show that EIV peps in IFA boosted plaque reduction titer after a single primary vaccine inoculation better than subsequent vaccine boosts. In addition, EIV peps in Halvogen boosted as well as vaccine boosts although EIV peps without adjuvant did not. Pooled sera from groups I, II, and III all showed at least a fourfold rise in titer over pooled sera from animals receiving no boost (group V). A fourfold titer increase is generally regarded as "seroconversion" in the evaluation of vaccine preparations. Similar results may be obtained when the plaque reduction titer against EIV-A2 is analyzed.

In a converse experiment, 8-week-old female Balb/C mice received a single intramuscular injection of a mixture containing 15 μg of each of the above peptides in complete Freund's adjuvant, while controls received similar inoculations of a heterologous peptide derived from unrelated viral sources (bovine viral diarrhea virus, or BVDV). Three weeks later, the mice received $10^5$ pfu of UV-irradiated EIV-A1 or EIV-A2 intramuscularly in incomplete Freund's adjuvant. The animals were bled six days after the second inoculation and the sera analyzed as above. The results are shown in Table 6.

TABLE 6

| Animal no. and initial treatment | Plaque reduction titer (EIV-A1) |
| --- | --- |
| 7D (EIV peps) | 1/40 |
| 7A (EIV peps) | >1/10* |
| 8B (BVD peps) | <1/10 |
| 8A (BVD peps) | <1/10 |
| 9B 0 | <1/10 |

*Assay not carried beyond 1/10 dilution.

These results show that the EIV peptides can also specifically prime the immune system of an animal for a subsequent inoculation of whole virus whereas an injection of heterologous peptide does not. Similar results may be obtained against EIV-A2.

D.4. Preparation of Recombinant Vaccinia Viruses Bearing Equine Influenza Antigens Methods described by Mackett, et al (supra), were used to insert H7, H3, N7, and N8 into vaccinia carrier.

Each cDNA was first subcloned into pGS20 which contains the 7.5 k vaccinia gene promoter with unique BamHI and SmaI sites immediately downstream for the insertion of the desired heterologous gene, and flanked by vaccinia thymidine kinase (TK) gene. The tk-gene permits homologous recombination into the vaccinia genome and affords a method of selection (generation of tk-viruses).

The constructions of the intermediate pGS20 derivative vectors containing EIV inserts are shown in FIG. 6 and are described below. The nucleotide numbering referred to in the text corresponds to that in FIGS. 1–4. In order to place the initiation codons of each EIV cDNA as close to the vaccinia promoter as possible and to prevent possible interference with processing, the cDNAs were prepared for insertion by removal of homopolymeric dC or dG tracts that were generated during cDNA cloning and by providing convenient restriction sites proximal to the 5' and 3' ends.

For H7, the H7 cDNA was cloned into the PstI site of M13mp7, thus generating a SalI site at the 3' end of the DNA. A BamHI site was placed 3 nucleotides before the ATG start codon by converting the nucleotide at position 40 from A to C using site-specific mutagenesis. The H7 coding sequence was removed as a BamHI/SalI (blunted) fragment and cloned into the BamHI/SmaI digested pGS20.

For H3, nucleotides 1–94 and 1720–1797 were removed from H3 cDNA by digestion with AccI at the 5' end (GTCTAC) and BglI at the 3' end (GCCAAAAAGGC). The deleted sequences were replaced using synthetic oligomers which contained SmaI restriction sites 8 nucleotides 5' of the ATG and 3 nucleotides 3' to the H3 termination codon while retaining the same coding sequence as represented in FIG. 2. The resulting cDNA was removed as a SmaI/SmaI fragment and cloned into the SmaI site of pGS20.

For N7, the full-length cDNA was cloned into pUC9 so that a unique SmaI site was positioned at the 3' end. The upstream portion of the sequence was excised by treating with HindIII and EcoRI and inserted into HindIII/EcoRI digested M13mp9. This upstream sequence was modified to create an NdeI site by conversion of nnucleotides 56 from G to C and 58 from A to T using site-specific mutagenesis. The heteroduplex phage was digested with HindIII and EcoRI and the heteroduplex fragment was amplified in pBR322, then removed by treating with NdeI, blunting with Klenow, and digesting with EcoRI. The mutated excised fragment was ligated into SmaI/EcoRI digested pUC19. The SmaI site from pUC19 is destroyed by the ligation and a unique BamHI site 5' to the N7 ATG results. The modified N7 5' fragment was removed from pUC19 as a BamHI/EcoRI fragment and religated to the remainder of the N7 sequence contained in pUC9 at the unique EcoRI site. The desired sequence containing the entire N7 coding region was obtained as a BamHI/SmaI fragment and ligated into BamI/SmaI-digested pGS20.

For N8, the cDNA was cloned into the PstI site of pUC8, which placed a unique SmaI site 3' of the cDNA. A unique AhaIII site already exists in N8 3 nucleotides. 5' of ATG, and hence an AhaIII/SmaI digest generates a full-length cDNA which is blunt-end ligated into the SmaI site of pGS20.

The four vaccinia-EIV vectors described above are designated pGS20-H7, pGS20-H3, pGS20-N7, and pGS20-N8, or, collectively, pGS20-EIV. FIG. 6 shows the nucleotide sequence surrounding the coding region of each EIV cDNA inserted into the BamHI/SmaI cloning site of pGS20. The dotted line after each ATG represents the sequence described in FIGS. 1–4 to the terminal PstI cloning sites (after the poly-G tracts) with the exception of H3, which was modified as described in the text.

These recombinant vectors are transfected into cells infected with wild-type vaccinia virus, which was purchased from Wyeth Laboratories, Inc. (Marietta, PA) and plaque purified twice in CV-1 cells. A small aliquot of virus stock (0.1 ml) is diluted with an equal volume of trypsin (0.25 mg/ml) and incubated for 30 min at 37° C. with vortexing, followed by sonication to disperse any cell clumps. The virus is diluted to a concentration of $5 \times 10^4$ plaque-forming units per ml in phosphate-buffered saline (PBS) containing 0.2% bovine serum albumin (BSA) and penicillin/steptomycin. CV-1 cells are infected in monolayers on 60 mm plates with 1 ml vaccinia virus to give a multiplicity of infection of 0.05 pfu/cell. The virus inoculum is incubated on the cells for 2 hr at 37° C. with rocking.

The DNA for transformation is prepared as described in Graham, et al, *Virology* (1973) 52: 456; Stow, et al, *J Gen Virol* (1976) 33: 447; and Frost, et al, *Virology* (1978) 91: 39. Briefly, 5–10 82 g of plasmid (pGS20 derivative) DNA, and 1–2 μg wild-type vaccinia virus DNA are added to 1 ml to Hepes-buffered saline (0.14 molar NaCl, 5 mM KCl, 1 mM Na phosphate, 0.1% dextrose, 20 mM Hepes, pH 7.05), and 50 μl of 2.5 molar $CaCl_2$ is added. The solutions are mixed and left at room temperature for 30 min, and the desired precipitate of DNA forms in this time.

The virus inoculum is aspirated from the CV-1 cell layers, and 1 ml of the DNA precipitate is substituted and the layers left at room temperature for 30 min, after which 9 ml prewarmed Eagle's MEM containing 8% FBS is added. The layers are incubated for 3.5 hr at 37° C., before aspirating off the medium and replacing it with 10 ml fresh Eagle's MEM containing 8% FBS. The monolayers are then left at 37° C. for 2 days, resulting in the devlopment of vaccinia cytopathic effects. The cells and virus are harvested by scraping, spun down, and resuspended in 0.5 ml Eagle's MEM and frozen at −20° C.

The resuspended virus/cell pellets are freeze-thawed three times by freezing the cells at −20° C. for 30 minutes and quickly thawing them at 37° C., followed by sonication for one minute to disperse the virus/cell clumps. The resulting crude virus stock is then inoculated in serial 10-fold dilutions onto 143 cells (Mackett, M., et al, *J Virol* (1984) 49: 857–864), a human tk- cell line. After two hours at 37° C., the 143 monolayers are then overlaid with 1% agarose containing 1× modified Eagle's medium, 5% fetal bovine serum, and 25 μg/ml 5-bromodeoxyuridine (BUdR). After incubation for two days at 37° C., BUdR-resistant plaques are picked and grown for 48 hours at 37° C. in 24 well plates of 143 cell monolayers in the presence of 25 μg/ml BUdR.

Virus is harvested and assayed for the presence of the EIV-derived gene by DNA-DNA dot blot hybridization, as follows: cells are scraped from the dish into an Eppendorf centrifuge tube, centrifuged for 1 minute, and the cell pellet resuspended in 0.2 ml PBS. After freeze-thawing 3 times and sonicating as described above, the sonicate is applied to a nitrocellulose filter and air dried. A wild-type virus control is also spotted onto the same filter. The filter is then placed on paper soaked in (1) 0.5M NaOH, (2) 1M Tris-HCl, pH 7.5, and (3) 2× SSC, for 5 minutes each. The filter is then baked at 80° C. under vacuum for 2 hours. The baked filter is prehybridized for 1–4 hours at 42° C. in 5 ml 50% formamide, 4× SSC, 5× Denhardt's solution, and 0.1 mg/ml sheared and boiled salmon sperm DNA. The filter is then hybridized overnight at 42° C. to 2× $10^7$ cpm of $^{32}$P-labeled EIV probe in 5 ml prehybridization buffer. The probe is prepared by isolating 5 μg of EIV gene insert from one of the pGS20-derivative vectors and nick translating the DNA using a commercially available nick translation kit. The filter is then washed twice for 30 minutes in 0.5× SSC, 0.1% SDS, air dried, and autoradiographed overnight at −70° C.

Virus containing EIV gene inserts by dot blot hybridization are infected onto monolayers of 143 cells and left until a confluent cytopathic effect is obtained. The culture medium is then aspirated off and the cells lysed in 1% SDS, 0.1M β-mercaptoethanol, 50 mM Tris-HCl, pH 7.8. The lysate is made 0.5 mg/ml in proteinase K, incubated 4 hours at 37° C., phenol extracted, ethanol precipitated, and analyzed by restriction enzyme analysis to show that the vaccinia genomes indeed contain the desired EIV genes.

The recombinant vaccinia so generated were designated vac-H7, vac-H3, vac-N7 and vac-N8 or collectively, vac-EIV.

D.5 Expression of EIV Surface Antigens by Vaccinia Recombinants

Each vac-EIV recombinant was plaqued separately onto CV1 monolayers. The monolayers were washed, fixed, and incubated with rabbit anti-EIV-A1 (for vac-H7 and vac-N7) and rabbit anti-EIV-A2 (for vac-H3 and vac-N8). Antibody binding specifically to EIV surface antigens was detected by a subsequent incubation with $^{125}$I-labeled staphylococcal A protein followed by autoradiography. In each case, all recombinant virus plaques bound the appropriate antibody.

Immunoprecipitation of $^{35}$S-labeled cellular lysates obtained from monolayers of CV1 cells infected by individual vac-EIV recombinants showed the presence of EIV protein. In the case of each recombinant virus, antisera raised against the appropriate whole virus immunoprecipitated a characteristic hemagglutinin or neuraminidase molecule identified by polyacrylamide gel electrophoresis and autoradiography.

D.6 Amplification of Vaccinia Recombinants

After the vac-EIV recombinants were identified as both carrying the appropriate EIV gene and expressing the encoded EIV protein, a single plaque of each is isolated ×2 in 143 cells in the presence of BUdR. The twice purified isolate is amplified once in 143 cells in the presence of BUdR and subsequently in CV-1 cells in the absence of selective pressure. The resulting vac-EIV recombinants are stable genetically and can be further amplified in CV-1 cells.

D.7 Bioassay of Vaccinia Recombinants

Horses are used as subjects to assess the ability of the recombinant vaccinia to raise titers of neutralizing anti-EIV antibodies in serum.

In general, pairs of horses are inoculated with wild-type or recombinant virus by intradermal administration of 1–2× $10^8$ plaque-forming units distributed in 2–3 sites on the back, and are bled at days 0, 14, and 28. The sera are then tested for the presence of anti-EIV neutralizing antibodies in the plaque reduction assay of ¶C.7.

In one experiment, four horses, 1–3 years old, housed in a P3 facility at Washington State University, Pullman, Wash., were ascertained to be serum negative with respect to anti-EIV antibodies, but were otherwise undocumented with respect to exposure. Control and test virus were administered intradermally by scarification with a needle to bleeding at four locations on the animals' necks. Each animal received a total of $10^8$ pfu of each indicated virus in a total of 0.4 ml (0.1 ml at each scar). VSV was used as a control; test viruses were H7, H3, N7, and N8, as described above ¶D.4).

The animals were bled at day 0 (preimmune), and at days 7, 14, and 21, and their sera assessed for neutralizing antibodies against each of EIV-A1 and EIV-A2 using the plaque reduction assay described in ¶C.7 hereinabove. The results, shown below in Table 7, indicate that while control VSV was not able to raise antiserum against EIV, all combinations of recombinant vaccinia containing DNA encoding H and/or N peptides, were able to do so.

TABLE 7

| Horse | Vaccine | EIV Strain | Day 0 | Day 7 | Day 14 | Day 21 |
|---|---|---|---|---|---|---|
| Lola | VSV | A1 | 1/10 | 1/10 | 1/10 | 1/10 |
|  |  | A2 | <1/10 | <1/10 | <1/10 | <1/10 |
| Howard | N7,N8 | A1 | 1/10 | 1/20 | 1/160 | 1/160 |
|  |  | A2 | <1/10 | 1/40 | 1/160 | 1/160 |
| Fanny | H7,H3 | A1 | <1/10 | 1/160 | 1/320 | 1/160 |
|  | N7,N8 | A2 | <1/10 | 1/320 | 1/640 | 1/320 |
| Leo | H7,H3 | A1 | <1/10 | 1/800 | 1/1600 | 1/800 |
|  |  | A2 | <1/10 | 1/640 | 1/1280 | 1/640 |

The results are maximum serum dilutionss able to reduce EIV pfu by 50%. The results for Leo at days 7, 14, and 21 are based on an initial serum dilution of 1/50 rather than the 1/10 dilution used for all other results.

We claim:

1. A recombinant DNA sequence encoding equine hemagglutinin H7 as depicted in FIG. 1.

2. A recombinant DNA sequence encoding equine neuraminidase N7 as depicted in FIG. 3.

* * * * *